US012569254B2

(12) United States Patent
Miraki et al.

(10) Patent No.: US 12,569,254 B2
(45) Date of Patent: Mar. 10, 2026

(54) CLIP WITH OPPOSED JAWS FOR LEFT ATRIAL APPENDAGE CLOSURE

(71) Applicant: EDWARDS LIFESCIENCES CORPORATION, Irvine, CA (US)

(72) Inventors: Manouchehr A. Miraki, Laguna Hills, CA (US); Jaime L. Baluyot, Westminster, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 97 days.

(21) Appl. No.: 18/433,243

(22) Filed: Feb. 5, 2024

(65) Prior Publication Data

US 2024/0173035 A1     May 30, 2024

Related U.S. Application Data

(63) Continuation of application No. PCT/US2022/039914, filed on Aug. 10, 2022.

(60) Provisional application No. 63/231,427, filed on Aug. 10, 2021.

(51) Int. Cl.
| | |
|---|---|
| *A61B 17/122* | (2006.01) |
| *A61B 17/00* | (2006.01) |
| *A61B 17/128* | (2006.01) |

(52) U.S. Cl.
CPC .... *A61B 17/1227* (2013.01); *A61B 17/00234* (2013.01); *A61B 17/1285* (2013.01); *A61B 2017/00243* (2013.01)

(58) Field of Classification Search
CPC .............. A61B 17/122; A61B 17/1227; A61B 2017/00243; A61B 17/12122; A61B 17/12022; A61B 17/12031; A61B 17/12109
See application file for complete search history.

(56) References Cited

U.S. PATENT DOCUMENTS

| | | | |
|---|---|---|---|
| 2014/0142597 A1* | 5/2014 | Winkler | ............. A61B 17/1227 606/157 |
| 2015/0223813 A1* | 8/2015 | Williamson, IV | ..... A61B 17/10 606/158 |
| 2019/0231356 A1* | 8/2019 | Deville | ............. A61B 17/1285 |
| 2020/0197014 A1 | 6/2020 | Deville et al. | |
| 2020/0345375 A1 | 11/2020 | Deville et al. | |

FOREIGN PATENT DOCUMENTS

| | | |
|---|---|---|
| EP | 3821826 A1 | 5/2021 |
| WO | 2007124579 A1 | 11/2007 |

* cited by examiner

*Primary Examiner* — Katherine M Shi

(74) *Attorney, Agent, or Firm* — Snell & Wilmer

(57) ABSTRACT

A clip may be configured to close the portion of the heart, to reduce blood flow therethrough as well as passage of clots or other undesired materials. The clip may be configured to close the left atrial appendage (LAA). The closure of the LAA may reduce the possibility of stroke or other maladies stemming from fluid flow with the LAA. The clip may include a first jaw with a compression surface facing a compression surface of a second jaw.

20 Claims, 23 Drawing Sheets

304             302

300

306

308

310

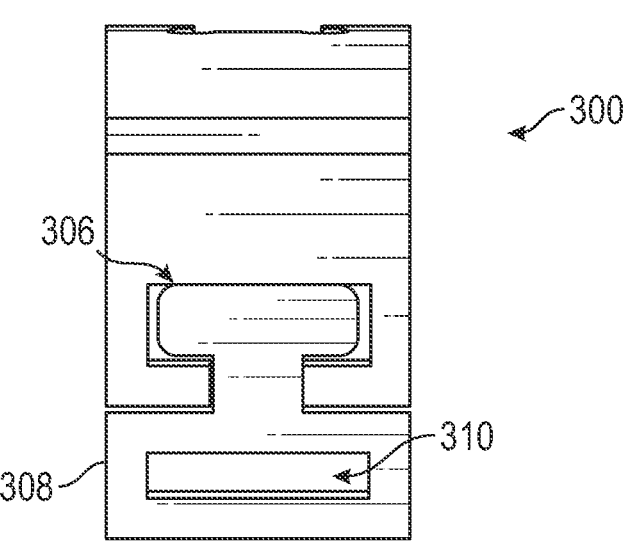
FIG. 30
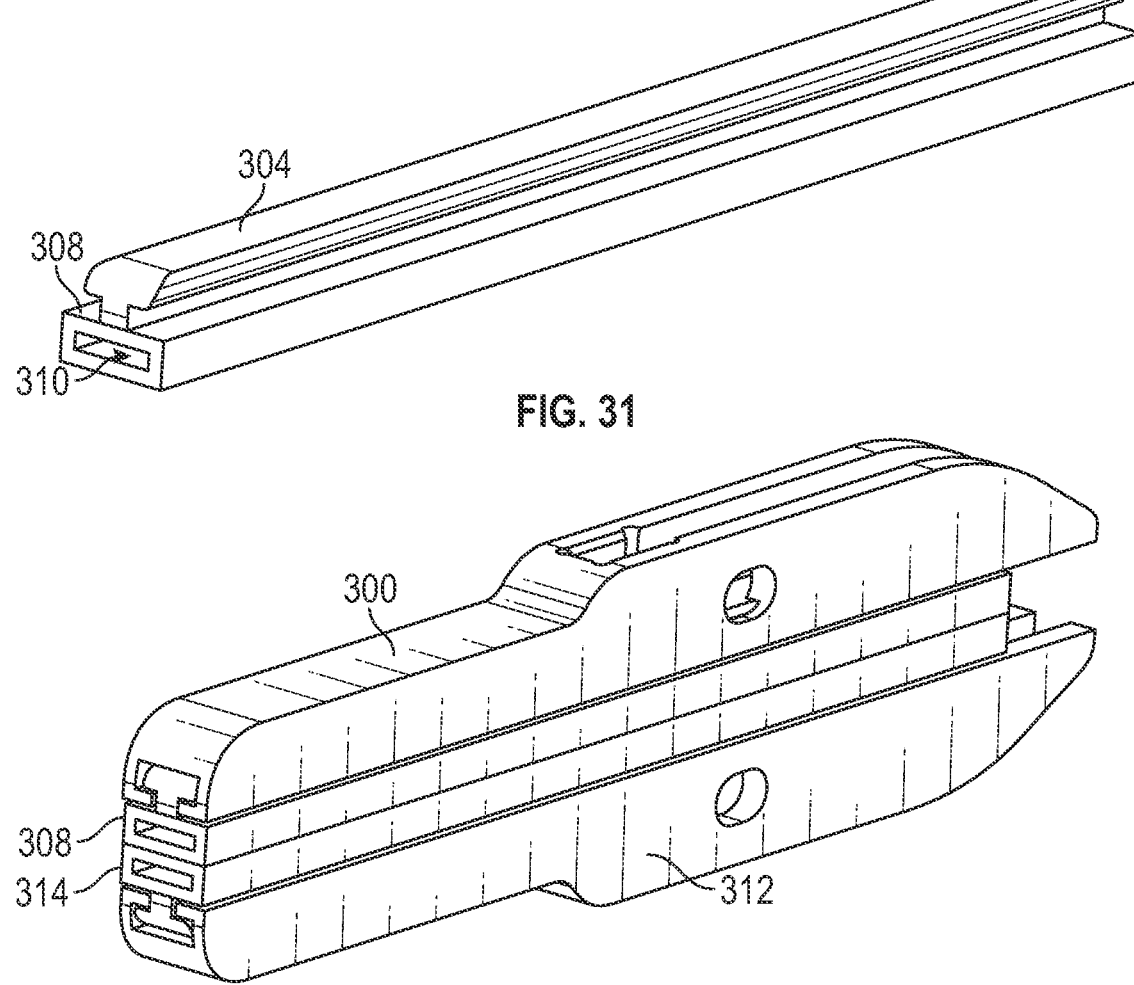
FIG. 31
FIG. 32

442          440

442          444

CLIP WITH OPPOSED JAWS FOR LEFT ATRIAL APPENDAGE CLOSURE

CROSS-REFERENCE TO RELATED APPLICATIONS

This application is a continuation of International Patent Application No. PCT/US2022/039914, filed Aug. 10, 2022, which claims the benefit of U.S. Patent Application No. 63/231,427, filed Aug. 10, 2021, the entire disclosures all of which are incorporated by reference for all purposes.

BACKGROUND

Field

Various examples disclosed herein relate generally to clips for medical implementation. Some examples relate to clips for a left atrial appendage (LAA).

Background

Cardiac arrhythmias are abnormal heart rhythms that can cause the heart to pump blood less effectively. Atrial fibrillation (AF) is one of the most common heart arrhythmia conditions. AF causes the left atrium to beat irregularly and reduces the efficiency of the "atrial kick" that helps to move blood into the left ventricle.

The left atrial appendage (LAA) is a muscular pouch located high on the free wall of the left atrium. The anatomy of the LAA is such that blood has a tendency to stagnate and form clots within the LAA. As blood flow is reduced with the progression of AF, the potential for clot formation increases tremendously.

Clots formed in the LAA can embolize into the bloodstream and move into the brain, where they can become lodged and eventually lead to stroke. It may be beneficial to close or occlude the LAA, to reduce the possibility of clots or other undesired materials from passing into the left atrium and into the bloodstream.

Left atrial appendage closure (also known as LAA closure or LAAC) is a minimally invasive procedure that is used to reduce the risk of stroke that comes as a result of atrial fibrillation.

SUMMARY

Systems, apparatuses, and methods disclosed herein may be directed to clips for medical implementation, including clips for a portion of a heart. The clips may be configured to close the portion of the heart, to reduce blood flow therethrough as well as passage of clots or other undesired materials. In examples, the clips may be configured to close the left atrial appendage (LAA). The closure of the LAA may reduce the possibility of stroke or other maladies stemming from fluid flow with the LAA. In examples, the clips may be positioned exterior of the LAA, to extend over an outer surface of the LAA for closure.

In aspects, a clip for a portion of a heart.

The clip may include a first jaw extending from a first end portion to a second end portion and including a compression surface and an outer surface facing opposite the compression surface.

The clip may include a second jaw extending from a first end portion to a second end portion and including a compression surface facing the compression surface of the first jaw and an outer surface facing opposite the compression surface of the second jaw.

The clip may include a spring extending over the outer surface of the first jaw and the outer surface of the second jaw and configured to force the first jaw and the second jaw together to compress the portion of the heart between the compression surface of the first jaw and the compression surface of the second jaw.

In aspects, a method may comprise deploying a clip to close a portion of a heart.

The clip may include a first jaw extending from a first end portion to a second end portion and including a compression surface and an outer surface facing opposite the compression surface.

The clip may include a second jaw extending from a first end portion to a second end portion and including a compression surface facing the compression surface of the first jaw and an outer surface facing opposite the compression surface of the second jaw.

The clip may include a spring extending over the outer surface of the first jaw and the outer surface of the second jaw and configured to force the first jaw and the second jaw together to compress the portion of the heart between the compression surface of the first jaw and the compression surface of the second jaw.

BRIEF DESCRIPTION OF THE DRAWINGS

FIG. 30 illustrates a distal end view of a jaw shown in FIG. 29.

FIG. 31 illustrates a perspective view of a cushion layer shown in FIG. 29.

FIG. 32 illustrates a perspective view of a clip.

DETAILED DESCRIPTION

Figures 1, 2:
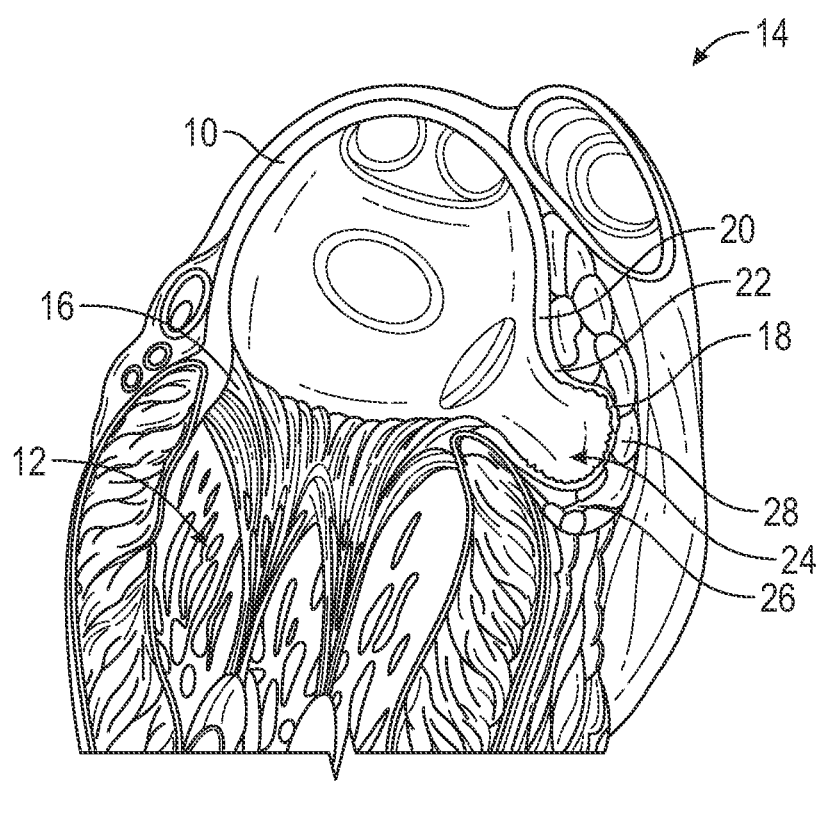
FIG. 1 shows a cross sectional schematic view of a portion of a heart.
FIG. 2 illustrates a perspective view of a clip.

FIG. 1 illustrates a cross sectional view of a left atrium 10 and a left ventricle 12 of an individual's heart 14. The left atrium 10 is configured to fill with blood to pass into the left ventricle 12 via the mitral valve 16 during the cardiac cycle. The left atrial appendage (LAA) 18 protrudes from the outer wall 20 of the left atrium 10 and includes an ostium 22 and a cavity 24 extending from the ostium 22. A LAA wall 26 may surround the cavity 24 and may form an outer surface 28 of the LAA 18. The LAA 18 has a pouch shape extending from the left atrium 10. The cavity 24 may be configured to fill with blood, allowing the LAA to serve as a decompression chamber during systole and when pressure otherwise increases in the left atrium 10.

In certain individuals, blood may stagnate and form clots within the LAA 18. Clots or other undesired materials stemming from the LAA 18 may travel into the bloodstream, producing a variety of maladies including strokes. It may thus be beneficial to close the LAA 18, to reduce the possibility of clots or other undesired material from producing such maladies.

Figure 3:
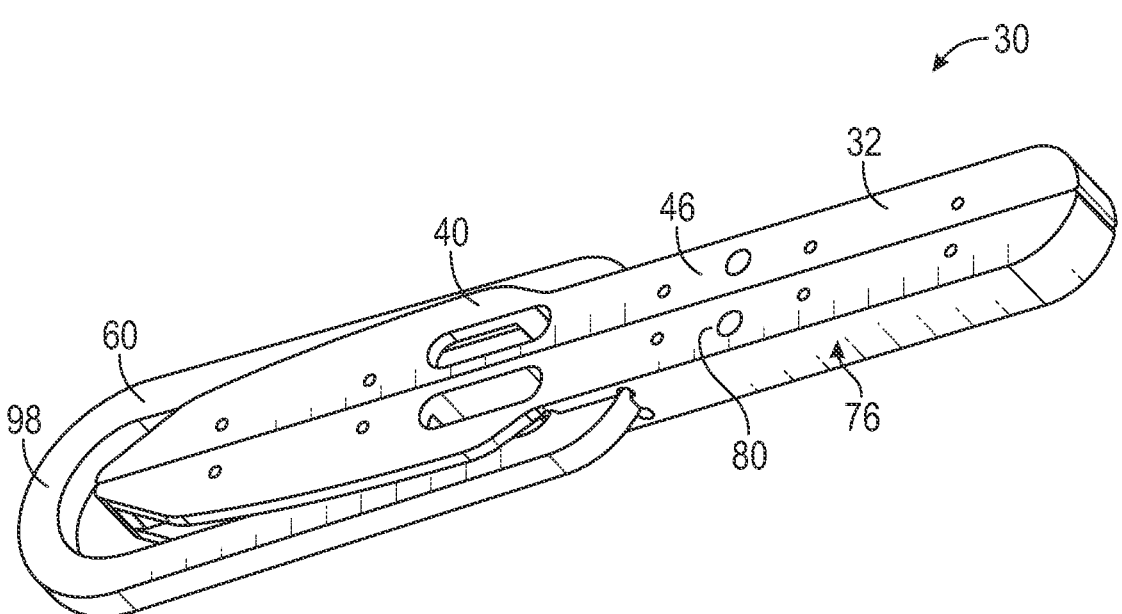
FIG. 3 illustrates a perspective view of the clip shown in FIG. 2 from an opposite side of the clip than shown in FIG. 2.

FIG. 2 illustrates an example of a clip 30 that may be utilized for a portion of a heart. FIG. 3 illustrates a side perspective view of the clip 30 opposite the side shown in FIG. 2. Referring to FIGS. 2 and 3, the clip 30 may be configured to close a LAA 18, to reduce the possibility of clots or other undesired materials stemming from the LAA 18 from traveling into the bloodstream.

The clip 30 may include a first jaw 32 and a second jaw 34. The first jaw 32 may extend from a first end portion 36 to a second end portion 38 and may have an elongate shape. The first jaw 32 may be configured as an elongate beam. The first jaw 32 may have a central portion 40 between the first end portion 36 and the second end portion 38.

The first jaw 32 may include four sides, including an outer surface 42, a compression surface (facing opposite the outer surface 42 and towards the second jaw 34), and two side surfaces 44, 46 (with side surface 46 shown in FIG. 3) each extending from the compression surface to the outer surface 42.

Figure 4:
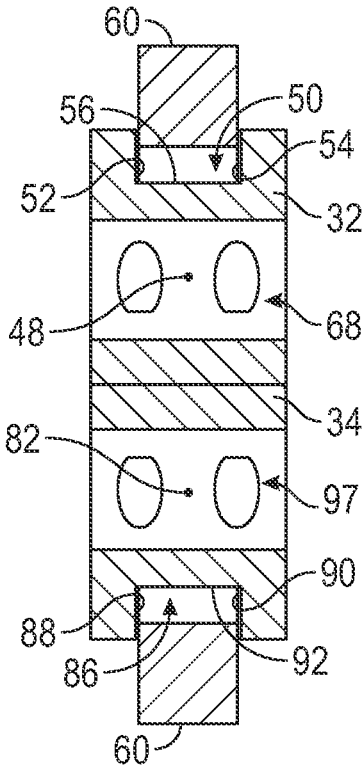
FIG. 4 illustrates a cross sectional view of the clip shown in FIG. 2 along line 4-4 in FIG. 2.

The first jaw 32 may extend along a longitudinal axis 48 (marked in FIGS. 4 and 6) and may have a rectangular cross section when viewed perpendicular to the longitudinal axis 48 (as visible in the cross sectional view of FIG. 4).

In examples, the first end portion 36 of the first jaw 32 may be tapered, such that a rounded tip 51 of the first jaw 32 is provided. The rounded tip 51 of the first jaw 32 may allow the first jaw 32 to be atraumatic to a patient's body upon insertion into the body and deployment to a desired location. In examples, the second end portion 38 of the first jaw 32 may be tapered.

Figures 5, 6:
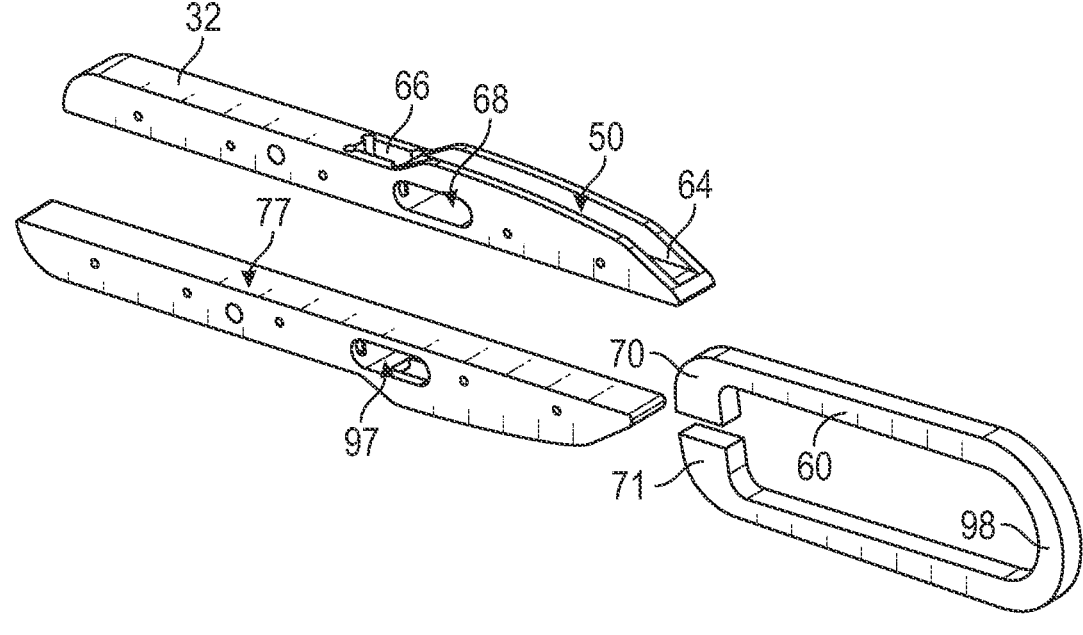
FIG. 5 illustrates an assembly view of the clip shown in FIG. 2.
FIG. 6 illustrates a cross sectional view of the clip shown in FIG. 2 along line 6-6 in FIG. 2.

The outer surface 42 of the first jaw 32 may include a channel 50. FIG. 4 illustrates a cross sectional view of the clip 30 along line 4-4 in FIG. 2, and FIG. 5 illustrates an assembly view of the clip 30, and FIG. 6 illustrates a cross sectional view of the clip 30 along line 6-6 in FIG. 2. Referring to FIGS. 4-6, the channel 50 may include a first side wall 52, a second side wall 54, and a lower wall 56 of the channel 50. The upper portion of the channel 50 may remain open for a spring 60 to pass through. The channel 50 may extend from the central portion 40 of the first jaw 32 to the second end portion 38 of the first jaw 32.

The channel 50 may include a first end 62 and a second end 64, with the second end 64 being opened to allow for the spring 60 to pass through.

A coupler 66 may be positioned at the first end 62 of the channel 50 and configured to receive an end of the spring 60. The coupler 66 may comprise a cavity in the first jaw 32 or may have another configuration as desired.

In examples, the first jaw 32 may include a recess 68 for receiving a device for applying an expansion force to the spring 60. The recess 68, as shown in FIG. 2, may be positioned between a first end 70 of the spring 60 and the second end portion 38 of the first jaw 32. The recess 68 may be positioned on one or more of the side surfaces 44, 46 and may extend through the first jaw 32 in examples as desired.

The second jaw 34 may extend from a first end portion 72 to a second end portion 74 and may have an elongate shape. The second jaw 34 may be configured as an elongate beam. The second jaw 34 may have a central portion 79 between the first end portion 72 and the second end portion 74.

The second jaw 34 may include four sides, including an outer surface 76 (marked in FIG. 3), a compression surface 77 (marked in FIG. 5 and facing opposite the outer surface 76 and towards the first jaw 32), and two side surfaces 78, 80 each extending from the compression surface to the outer surface 76. The compression surface 77 of the second jaw 34 faces the compression surface of the first jaw 32.

The second jaw 34 may extend along a longitudinal axis 82 (marked in FIGS. 4 and 6) and may have a rectangular cross section when viewed perpendicular to the longitudinal axis 82 (as visible in the cross sectional view of FIG. 4).

In examples, the first end portion 72 of the second jaw 34 may be tapered, such that a rounded tip 84 of the second jaw 34 is provided. The rounded tip 84 of the second jaw 34 may allow the second jaw 34 to be atraumatic to a patient's body upon insertion into the body and deployment to a desired location. In examples, the second end portion 74 of the second jaw 34 may be tapered.

The outer surface 76 of the second jaw 34 may include a channel 86. Referring to FIGS. 4-6, the channel 86 may include a first side wall 88, a second side wall 90, and a lower wall 92 of the channel 86. The upper portion of the channel 86 may remain open for the spring 60 to pass through. The channel 86 may extend from the central portion 79 of the second jaw 34 to the second end portion 74 of the second jaw 34.

The channel 86 may include a first end 94 and a second end 96, with the second end 96 being opened to allow for the spring 60 to pass through.

A coupler 99 may be positioned at the first end 94 of the channel 86 and configured to receive an end of the spring 60. The coupler 99 may comprise a cavity in the second jaw 34 or may have another configuration as desired.

In examples, the second jaw 34 may include a recess 97 for receiving a device for applying an expansion force to the spring 60. The recess 97, as shown in FIG. 2, may be positioned between a second end 71 of a spring 60 and the second end portion 74 of the second jaw 34. The recess 97 may be positioned on one or more of the side surfaces 78, 80 and may extend through the second jaw 34 in examples as desired.

In examples, the recess 97 of the second jaw 34 and the recess 68 of the first jaw 32 may be positioned to equally distribute the compression load from the spring 60 to the respective end portions 36, 38 and 72, 74 of the first jaw 32 and second jaw 34.

In examples, the recess 97 of the second jaw 34 and the recess 68 of the first jaw 32 may be configured to allow the clip 30 to be variably positioned relative to the device for applying the expansion force to the spring 60. For example, referring to FIG. 8A, the device for applying the expansion force to the spring 60 may comprise expandable arms 101, 103 including respective protrusions 105, 107. The arms 101, 103 may scissor with respect to each other or otherwise be configured to expand. The protrusions 105, 107 may be configured to fit within respective recesses 68, 97 to apply the expansion force to the spring 60 (with the protrusions 105, 107 moved in opposite directions to move the clip 30 to the opened state).

Figure 8A:
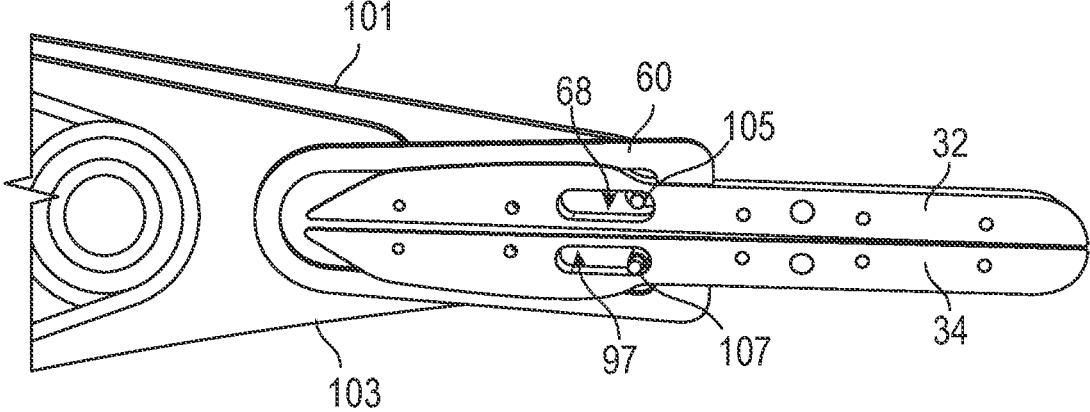
FIGS. 8A-8C illustrate a perspective view of variable positioning of the clip shown in FIG. 2.

As shown in FIG. 8A, with the protrusions 105, 107 both inserted into the recesses 68, 97 at the same longitudinal position along the recesses 68, 97, the clip 30 may be held parallel with the expandable arms 101, 103.

Figure 8B:
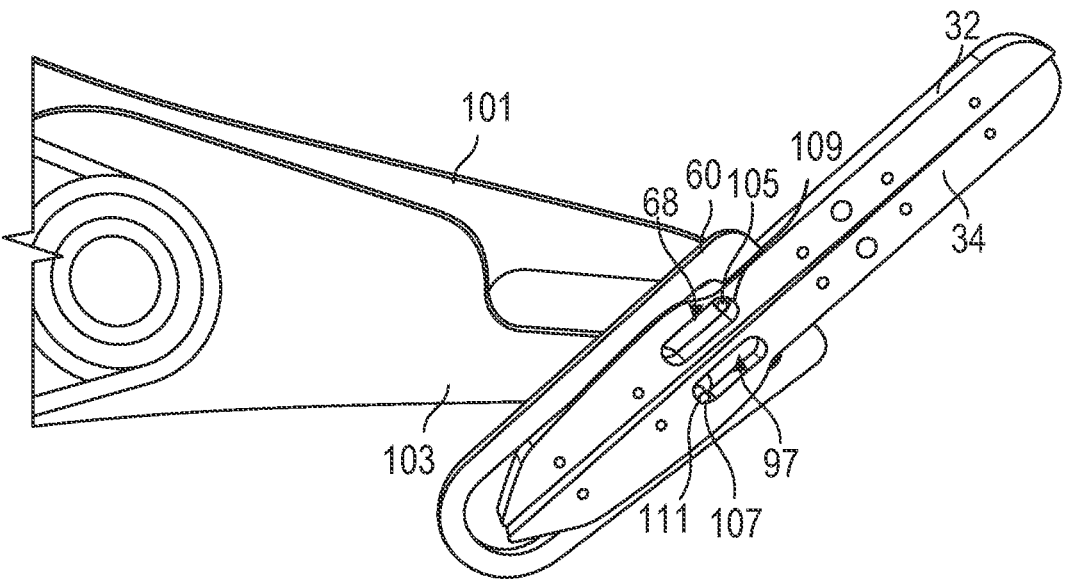

As shown in FIG. 8B, with the protrusion 105 at a first end 109 of the recess 68 and the protrusion 107 at an opposite second end 111 of the recess 97, the clip 30 may be pivoted and held at an angle with respect to the arms 101, 103. The angle may be a 45 degree angle or other angle as desired.

Figure 8C:
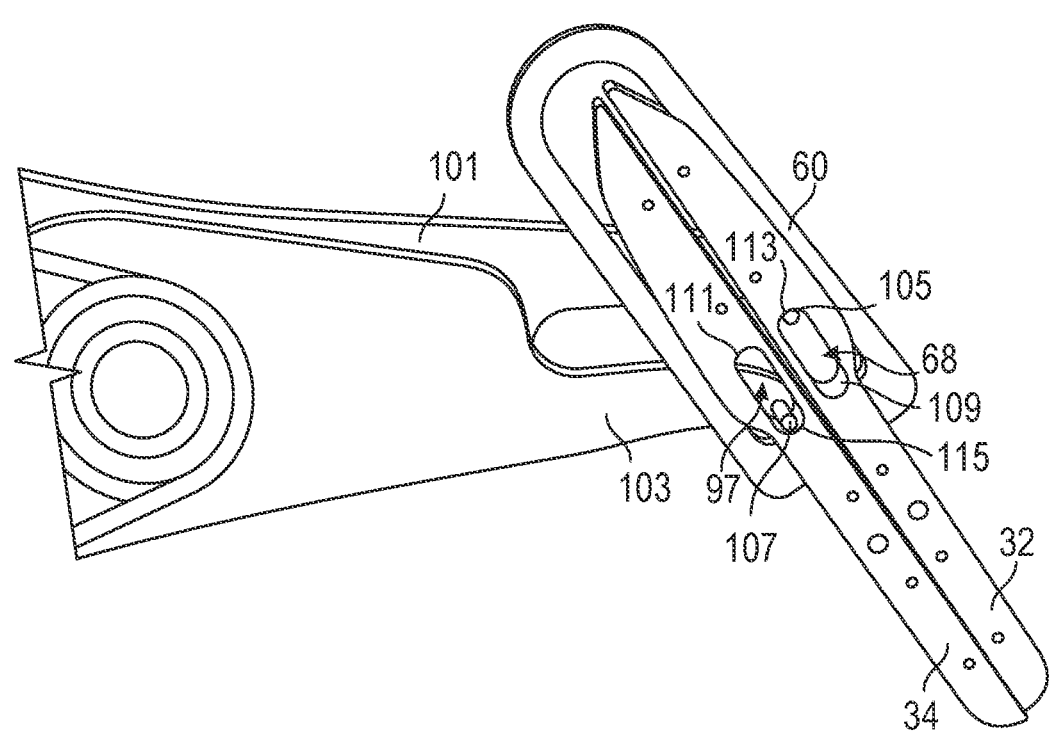

As shown in FIG. 8C, with the protrusion 105 at a second end 113 of the recess 68 and the protrusion 107 at an opposite first end 115 of the recess 97, the clip 30 may be pivoted and held at an angle with respect to the arms 101, 103. The angle may be a 45 degree angle or other angle as desired and may be opposite the angle shown in FIG. 8B. The angle shown in 8B, for example, may be a 45 degree up angle, and the angle shown in FIG. 8C may be a 45 degree down angle. The clip 30 accordingly may be pivoted with respect to the arms 101, 103 in an arc and held in position with respect to the arms 101, 103 at an angle if desired.

In examples, the compression surfaces of the jaws 32, 34 may be coated with a medical grade soft material to make the compression surfaces of the jaws 32, 34 atraumatic if desired.

Referring to FIG. 2, the spring 60 may extend over the outer surface 42 of the first jaw 32 and the outer surface 76 of the second jaw 34 and may be configured to force the first jaw 32 and the second jaw 34 together to compress the portion of the heart between the compression surface of the first jaw 32 and the compression surface 77 of the second jaw 34 (marked in FIG. 5). The spring 60, for example may have a "C" shape with a first end 70 and a second end 71 and a loop 98 coupled to the first end 70 and the second end 71. The loop 98 may include straight portions 95 coupled to a curved portion 93 forming the curve of the "C" shape. The first end 70 of the spring 60 may be coupled to the central portion 40 of the first jaw 32 and the second end 71 of the spring 60 may be coupled to the central portion 79 of the second jaw 34, and the loop 98 may extend towards the second end portion 38 of the first jaw 32 and the second end portion 74 of the second jaw 34.

The loop 98 may extend within the channel 50 of the first jaw 32 and the channel 86 of the second jaw 34. The loop 98 may protrude from the second end portion 38 of the first jaw 32 and the second end portion 74 of the second jaw 34. The loop 98 may be positioned within the channel 50 of the first jaw 32 and the channel 86 of the second jaw 34 between the respective side walls 52, 54 of the channel 50 and the side walls 88, 90 of the channel 86 (marked in FIG. 4). The loop 98 may be spaced from the respective lower walls 56, 92 of the channels 50, 86 such that the loop 98 may move towards the respective lower walls 56, 92 upon the clip 30 being in an opened state. The spring 60, for example, may pivot with respect to the lower walls 56, 92 upon the clip 30 being in an opened state.

The position of the loop 98 within the channels 50, 86 may allow for expansion of the clip 30. The position of the loop 98 within the channels 50, 86 may reduce the possibility of twisting of the spring 60 during opening or closing of the clip 30. The position of the loop 98 within the channels 50, 86 may allow the jaws 32, 34 to open further than in examples shown in FIGS. 9-11 for example.

The loop 98 may reside within the channels 50, 86 continuously and may reduce the possibility of the jaws 32, 34 from moving distally and side to side.

The spring 60 may extend within the plane of movement of the first jaw 32 and the second jaw 34.

The spring 60 may be configured to allow the clip 30 to move from an opened state to a closed state, yet force the clip 30 towards the closed state. The spring 60 accordingly may provide a force that moves the compression surfaces of the first jaw 32 and second jaw 34 towards each other to compress a portion of the heart therein. The spring 60 may be configured to keep the jaws 32, 34 under positive compression at all times, even at rest.

The spring 60 may have a "C" shape to allow the first end portions 36, 72 of the first jaw 32 and the second jaw 34 respectively to form an axial opening 100 (marked in FIG. 7A) for a space 102 (marked in FIG. 7A) between the first jaw 32 and the second jaw 34 for receiving the portion of the heart. The clip 30 may be positioned in an opened state and with the portion of the heart slid through the axial opening 100 and into the space 102. In examples, other methods of entry into the space 102 may be provided (e.g., along an axis of the LAA).

The loop 98 may form a boundary of the space 102 between the first jaw 32 and the second jaw 34. The loop 98 may protrude from the second end portion 38 of the first jaw 32 and the second end portion 74 of the second jaw 34. The loop 98 accordingly may prevent the clip 30 from sliding distally with respect to the LAA 18 upon deployment, and may prevent the tissue of the LAA 18 from protruding further than the loop 98 upon compression of the LAA 18.

Figure 7A:
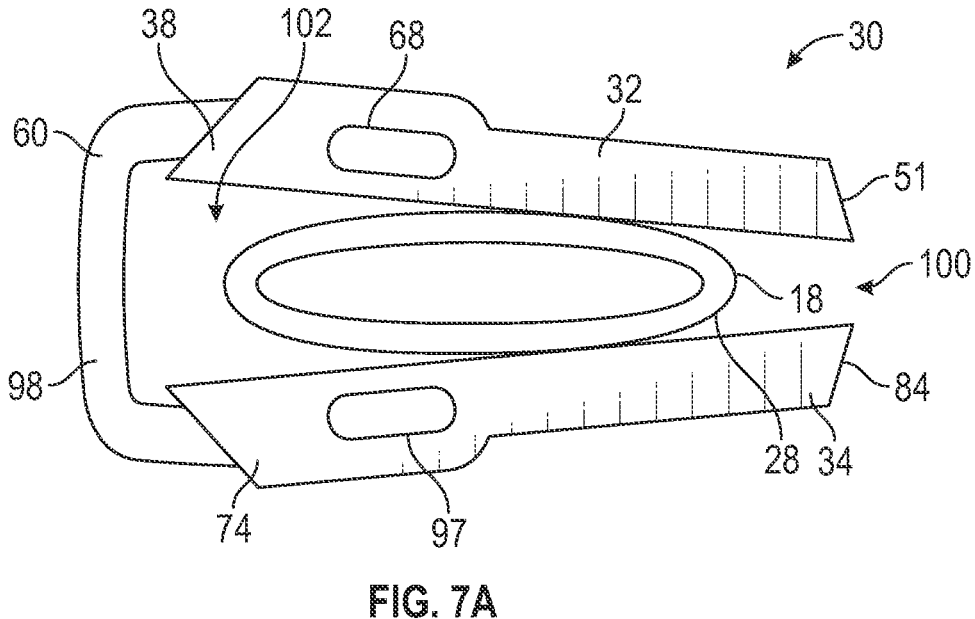
FIGS. 7A and 7B illustrate steps of a deployment of the clip shown in FIG. 2.

The spring 60 may be configured to pivotally couple to the couplers 66, 99. As such, upon the clip 30 being positioned in the opened state, the compressive surfaces of the first jaw 32 and second jaw 34 may be angled with respect to each other, with the tips 51, 84 positioned closer to each other than the second end portions 38, 74 of the jaws 32, 34 as shown in FIG. 7A. As such, upon closure of the clip 30, the tips 51, 84 may be configured to close earlier than the second end portions 38, 74 of the jaws 32, 34. The spring 60 may pivotally couple to the couplers 66, 99 such that the second end portions 38, 74 of the first jaw 32 and second jaw 34 open prior to the tips 51, 84 upon opening of the clip 30. The spring 60 may pivotally couple to the couplers 66, 99 without need for a pin, or bonding or welding in examples.

In operation, the clip 30 may be utilized to close the LAA 18.

Figure 7B:
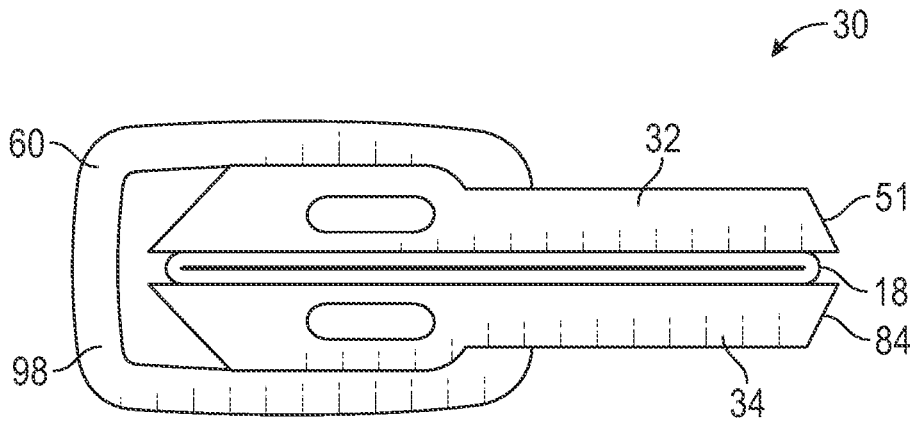

FIGS. 7A and 7B illustrate an exemplary deployment of the clip 30. Features of the clip 30 may be excluded from view in FIGS. 7A and 7B. In FIG. 7A, the clip 30 may be placed in an opened state and moved towards the LAA 18 in a direction transverse to the main axis of the LAA 18. In examples, other approaches (e.g., along the main axis of the LAA 18) may be utilized as desired. Access may be provided to the LAA 18 in a variety of manners, including a trans-catheter access or a surgical access such as a thoracotomy, mini thoracotomy, or other methods of access.

The clip 30 may be placed over the outer surface 28 of the LAA 18. In examples, a delivery apparatus may be utilized to move the clip 30 towards the LAA 18, or in examples, a user (e.g., a medical technician such as a surgeon, or other form of medical technician) may manually place the clip 30. The delivery apparatus, for example, may comprise a device for applying an expansion force to the spring 60, and may insert into the respective recesses 68, 97 of the first jaw 32 and the second jaw 34 to retain the clip 30 in the opened state. The device may include expandable arms for entering the respective recesses 68, 97 in examples, among other forms of devices.

The clip 30 may be placed over the outer surface 28 of the LAA 18 in an opened state. A user may confirm a desired placement of the clip 30 over the LAA 18.

In FIG. 7B, the clip 30 may be moved to a closed state with the LAA 18 compressed between the first jaw 32 and the second jaw 34. The device for applying the expansion force to the spring 60 may reduce the expansion force to allow the clip 30 to close, and the device may be removed from the clip 30. The spring 60 may force the clip 30 to the closed state. The entire span of the LAA 18 may be closed as desired at the ostium or another portion of the LAA 18 may be closed. The clip 30 may be closed with the tips 51, 84 closing earlier than the second end portions 38, 74 of the jaws 32, 34. Such a feature may reduce the possibility of tissue of the LAA 18 protruding from the tips 51, 84 of the jaws 32, 34 during closure. The jaws 32, 34 may rotate with respect to the spring 60 to place the jaws 32, 34 parallel with each other. The spring 60 may slide outward in the respective channels 50, 86 upon rotation of the jaws 32, 34.

In examples, if desired, the clip 30 may be opened and either removed or repositioned in a deployment procedure or another procedure. The clip 30 may be grasped and the force of the spring 60 may be overcome to open the clip 30.

The clip 30 may be utilized to close the LAA 18, yet in examples other portions of a heart may be clipped or closed via use of the clip 30. In examples, other portions of a body, such as a tubular vessel or other portions of a body may be closed with the clip 30. Deployment may be via a delivery apparatus or via another method as desired.

Variations in the configuration of the clip 30 may be provided as desired.

Figure 9:
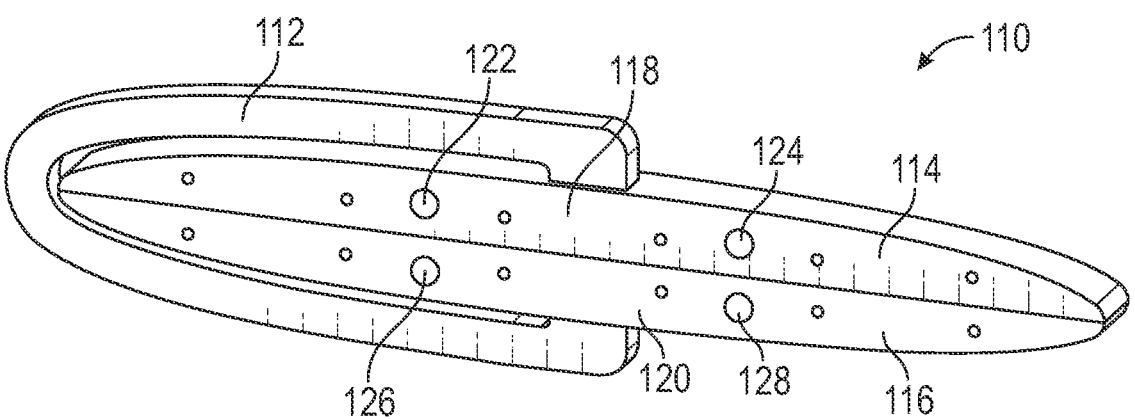
FIG. 9 illustrates a perspective view of a clip.

FIG. 9, for example, illustrates an example of a clip 110 in which the spring 112 does not extend within a channel and extends entirely outside of the first jaw 114 and the second jaw 116. The spring 112 couples to a respective central portion 118, 120 of the first jaw 114 and the second jaw 116. The first jaw 114 may include one or more recesses 122, 124 for receiving a device for applying an expansion force to the spring 112, and the second jaw 116 may include one or more recesses 126, 128 for receiving a device for applying an expansion force to the spring 112. The device may be utilized to retain the clip 110 in an opened state.

Figures 10, 11:
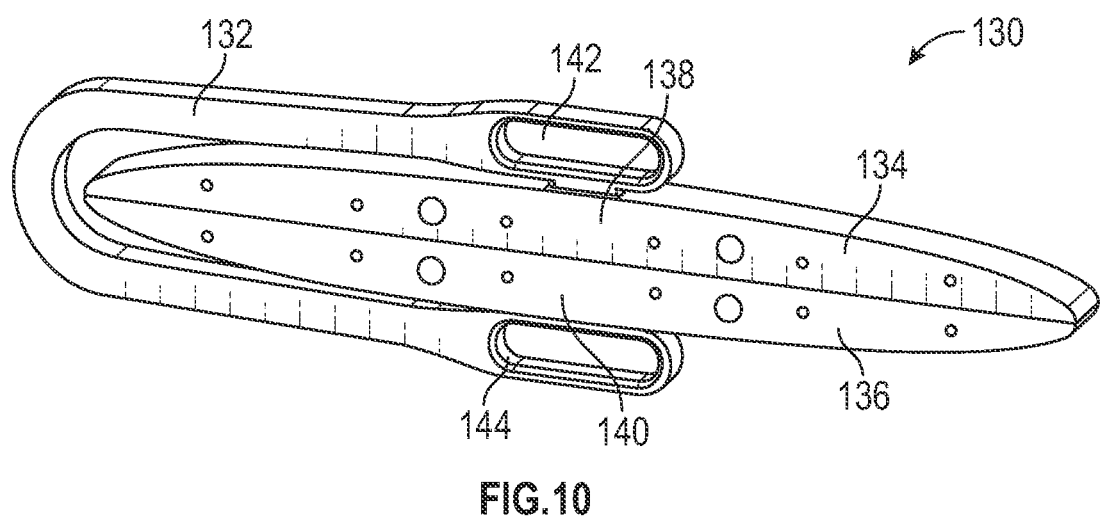
FIG. 10 illustrates a perspective view of a clip.
FIG. 11 illustrates a perspective view of a clip.

FIG. 10 illustrates an example of a clip 130 in which the spring 132 does not extend within a channel and extends entirely outside of the first jaw 134 and the second jaw 136. The spring 132 couples to a respective central portion 138, 140 of the first jaw 134 and the second jaw 136. The spring 132 may include one or more recesses 142, 144 for receiving a device for applying an expansion force to the spring 132. The device may be utilized to retain the clip 130 in an opened state.

FIG. 11 illustrates an example of a clip 150 in which the spring 152 does not extend within a channel and extends entirely outside of the first jaw 154 and the second jaw 156. The spring 152 couples to a respective central portion 158, 160 of the first jaw 154 and the second jaw 156. The first jaw 154 may include a recess 162 for receiving a device for applying an expansion force to the spring 112. The recess 162 may pass partially through a side surface of the first jaw 154. The second jaw 156 may include a recess 164 for receiving a device for applying an expansion force to the spring 112. The recess 164 may pass partially through a side surface of the second jaw 156. The device may be utilized to retain the clip 150 in an opened state.

In the examples shown in FIGS. 2-11, the jaws may be preloaded by the respective springs. The jaws may be configured to be at rest in a closed state and may require a force to open the jaws.

Various other modifications of the clips disclosed herein may be provided. Various other methods of deployment and use of the clips may be provided as desired.

FIGS. 12-17 illustrate an example of a clip 170 for a portion of a heart. The clip 170 may include similar features as the clip 30 shown in FIGS. 2-8C. Features of the clip 30 may apply to the clip 170 shown in FIGS. 12-17 unless stated otherwise. The clip 170 may include a first jaw 172, a second jaw 174, and a spring 176. The spring 176 may be configured to force the first jaw 172 and the second jaw 174 together to compress a portion of the heart between a compression surface of the first jaw 172 and a compression surface of the second jaw 174.

The first jaw 172 may extend from a first end portion 177, or distal end portion, to a second end portion 179, or proximal end portion, of the first jaw 172. The first jaw 172 may include a central portion 173 between the first end portion 177 and the second end portion 179 of the first jaw 172. The second end portion 179 of the first jaw 172 may be tapered in examples.

The first jaw 172 may include a first side surface 178 configured to face a first side direction of the first jaw 172 and may include a second side surface 180 (marked in FIG. 15) that faces a second side direction that is opposite the first side direction. The first jaw 172 may include a compression surface 184 (marked in FIG. 16) and an outer surface 182 facing opposite the compression surface 184. The first side surface 178 may extend from the compression surface 184 to the outer surface 182 of the first jaw 172.

One or more of the side surfaces 178, 180 may include a recess 181 for receiving a device for applying an expansion force to the spring 176, as disclosed herein.

Figure 12:
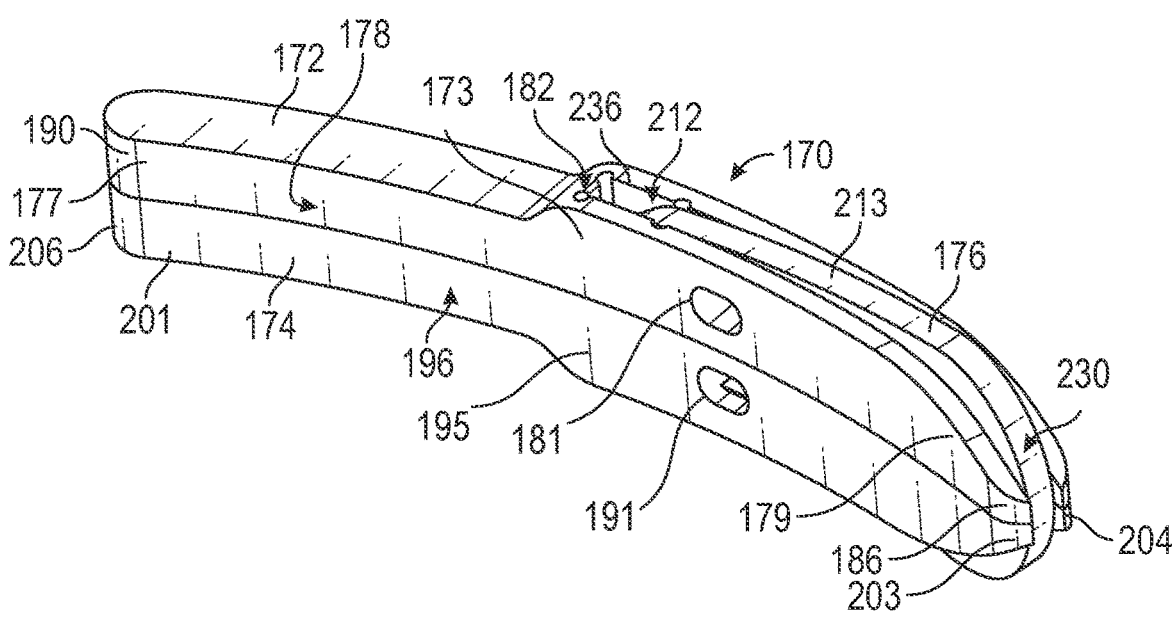
FIG. 12 illustrates a top front perspective view of a clip.

The first side surface 178 of the first jaw 172 may have a curvature. The first side surface 178 may be curved concave with respect to the first jaw 172, as shown in FIG. 12 for example. The first side surface 178 may be curved concave from a proximal tip 186 at a second end portion 179 or proximal end portion of the first jaw 172 to a distal tip 190 at a first end portion 177 or distal end portion of the first jaw 172. In examples, the concave curvature may be a constant curvature from a proximal tip 186 to a distal tip 190 of the first jaw 172. For example, the curvature of the first side surface 178 may include a constant radius of curvature (e.g., about 13 cm (about 5 inches), about 15 cm (about 6 inches), about 18 cm (about 7 inches), or a greater or lesser radius of curvature as desired). In examples, other configurations of the first side surface 178 or other curvatures may be provided. For example, a varied curvature may be provided or portions lacking a curvature (e.g., flat portions) may be provided, among other configurations.

Figure 13:
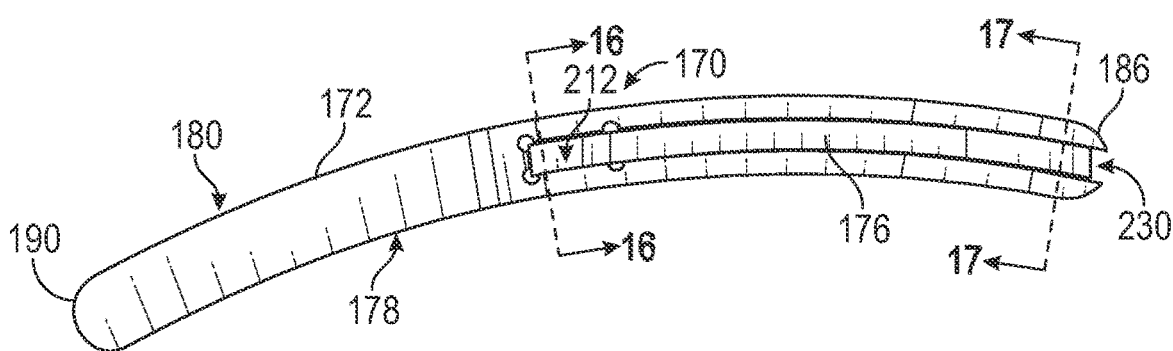
FIG. 13 illustrates a top view of the clip shown in FIG. 12.

The second side surface 180 of the first jaw 172 may have a curvature. The second side surface 180 may be curved convex with respect to the first jaw 172, as shown in FIG. 13 for example. The first side surface 178 may be curved convex from a proximal tip 186 at a second end portion 179 or proximal end portion of the first jaw 172 to a distal tip 190 at a first end portion 177 or distal end portion of the first jaw 172. In examples, the convex curvature may be a constant curvature from a proximal tip 186 at a second end portion 179 or proximal end portion of the first jaw 172 to a distal tip 190 at a first end portion 177 or distal end portion of the first jaw 172. For example, the curvature of the second side surface 180 may include a constant radius of curvature (e.g., about 13 cm (about 5 inches), about 15 cm (about 6 inches), about 18 cm (about 7 inches), or a greater or lesser radius of curvature as desired). In examples, other configurations of the second side surface 180 or other curvatures may be provided. For example, a varied curvature may be provided or portions lacking a curvature (e.g., flat portions) may be provided, among other configurations.

In examples, the first side surface 178 may have a concave curvature with respect to the first jaw 172 and the second side surface 180 may have a convex curvature with respect to the first jaw 172. In examples, the curvature of the first side surface 178 and the second side surface 180 may match each other such that the arcs of the first side surface 178 and the second side surface 180 remain parallel as such in FIG. 13. In examples, different curvatures may be provided for the first side surface 178 and the second side surface 180 (e.g., both surfaces being concave or convex, or both surfaces having different curvatures than each other).

The curvature of the first side surface 178 and the second side surface 180 may be in a plane 194 (marked in FIG. 14) that may be transverse or perpendicular to a plane of closure of the clip 170. The first jaw 172 may curve towards a side direction that is transverse to the longitudinal extent of the first jaw 172.

The second jaw 174 may extend from a first end portion 201, or distal end portion, to a second end portion 203, or proximal end portion, of the second jaw 174. The second jaw 174 may include a central portion 195 between the first end portion 201 and the second end portion 203 of the second jaw 174. The second end portion 203 of the second jaw 174 may be tapered in examples.

The second jaw 174 may include a first side surface 196 configured to face a first side direction of the second jaw 174 and may include a second side surface 198 (marked in FIG. 15) that faces a second side direction that is opposite the first side direction. The side surface 196 may be referred to as a third side surface and the side surface 198 may be referred to as a fourth side surface in view of the side surfaces of the first jaw 172. The second jaw 174 may include a compression surface 202 (marked in FIG. 16) and an outer surface 200 facing opposite the compression surface 202. The first side surface 196 may extend from the compression surface 202 to the outer surface 200 of the second jaw 174.

One or more of the side surfaces 196, 198 may include a recess 191 for receiving a device for applying an expansion force to the spring 176, as disclosed herein.

The first side surface 196 of the second jaw 174 may have a curvature. The first side surface 196 may be curved concave with respect to the second jaw 174, as shown in FIG. 12 for example. The first side surface 196 may be curved concave from a proximal tip 204 at a second end portion 203 or proximal end portion of the second jaw 174 to a distal tip 206 at a first end portion 201 or distal end portion of the second jaw 174. In examples, the concave curvature may be a constant curvature from a proximal tip 204 to a distal tip 206 of the second jaw 174. For example, the curvature of the first side surface 196 may include a constant radius of curvature (e.g., 5 inches, 6 inches, 7 inches, or a greater or lesser radius of curvature as desired). In examples, other configurations of the first side surface 196 or other curvatures may be provided. For example, a varied curvature may be provided or portions lacking a curvature (e.g., flat portions) may be provided, among other configurations.

Figure 15:
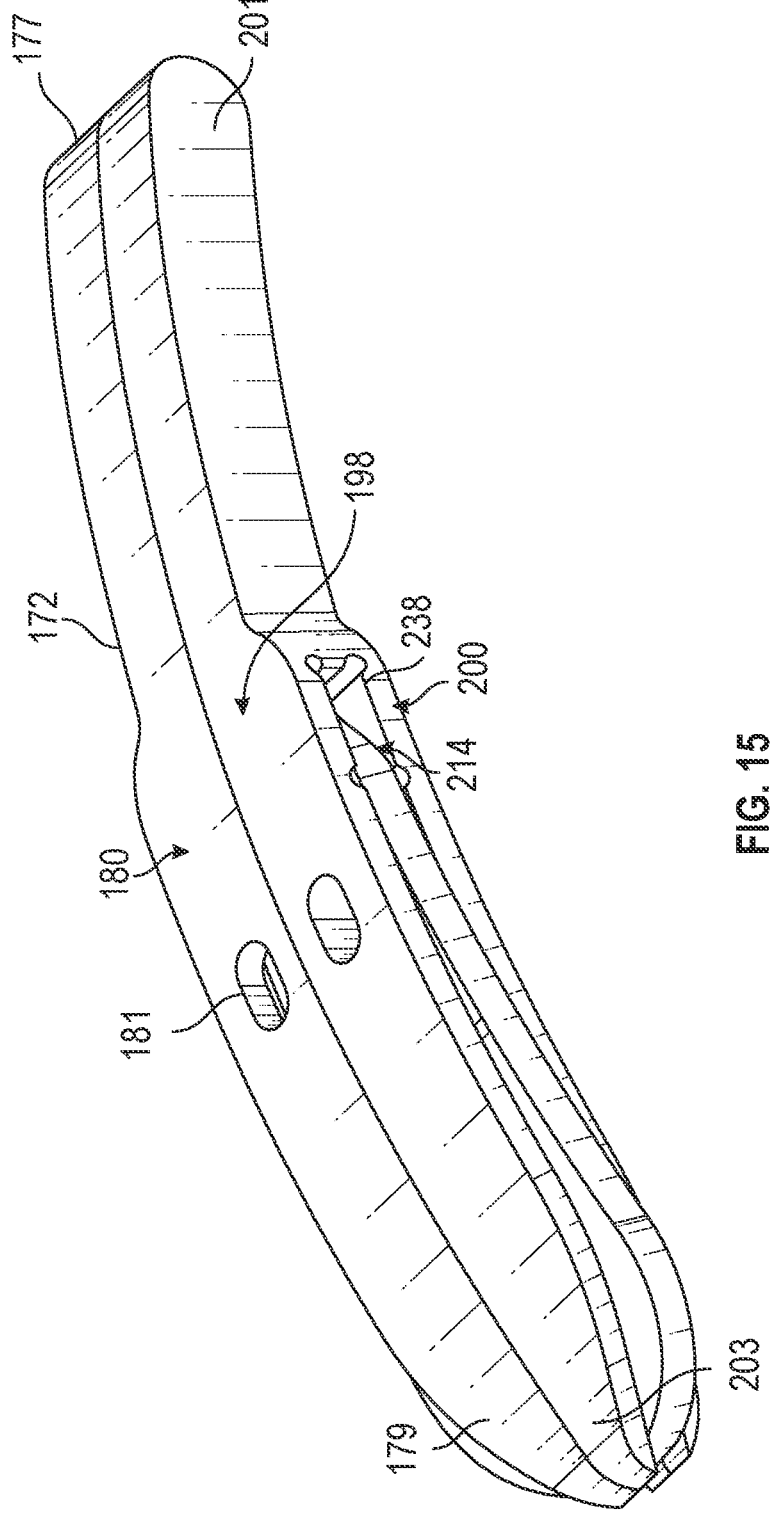
FIG. 15 illustrates a bottom rear perspective view of the clip shown in FIG. 12.

The second side surface 198 of the second jaw 174 may have a curvature. The second side surface 198 may be curved convex with respect to the second jaw 174, as shown in FIG. 15 for example. The second side surface 198 may be curved convex from a proximal tip 204 at a second end portion 203 or proximal end portion of the second jaw 174 to a distal tip 206 at a first end portion 201 or distal end portion of the second jaw 174. In examples, the convex curvature may be a constant curvature from a proximal tip 204 to a distal tip 206 of the second jaw 174. For example, the curvature of the second side surface 198 may include a constant radius of curvature a constant radius of curvature (e.g., about 13 cm (about 5 inches), about 15 cm (about 6 inches), about 18 cm (about 7 inches), or a greater or lesser radius of curvature as desired). In examples, other configurations of the second side surface 198 or other curvatures may be provided. For example, a varied curvature may be provided or portions lacking a curvature (e.g., flat portions) may be provided, among other configurations.

In examples, the first side surface 196 may be curved concave with respect to the second jaw 174 and the second side surface 198 may be curved convex with respect to the second jaw 174. In examples, the curvature of the first side surface 196 and the second side surface 198 may match each other such that the arcs of the first side surface 196 and the second side surface 198 remain parallel as shown in FIG. 13. In examples, different curvatures may be provided for the first side surface 196 and the second side surface 198 (e.g., both surfaces being concave or convex, or both surfaces having different curvatures than each other).

The curvature of the first side surface 196 and the second side surface 198 may be in a plane 210 (marked in FIG. 14) that may be transverse or perpendicular to a plane of closure of the clip 170. The second jaw 174 may curve towards a side direction that is transverse to the longitudinal extent of the second jaw 174.

The clip 170 may beneficially curve towards the side direction to allow the curvature of the clip 170 to contour to a shape of the left atrium 10 (marked in FIG. 1) upon occlusion of the ostium 22 of the LAA 18. As such, the concave curvatures of the first side surfaces 178, 196 of the jaws 172, 174 may face towards the left atrium 10 upon deployment to an ostium 22 of the LAA 18. Such a feature may reduce the possibility of pouches or other undesired areas forming along the occlusion line of the clip 170. Other benefits may result from a curved shape of a clip. In examples, the curvature of the clip 170 may match the curvature of the left atrium 10.

The outer surface 182 of the first jaw 172 may include a first channel 212 (marked in FIG. 16) that the loop 213 of the spring 176 extends within. The outer surface 200 of the second jaw 174 may include a second channel 214 (marked in FIG. 16) that the loop 213 of the spring 176 extends within. The loop 213 of the spring 176 may extend towards the second end portions 179, 203 of the respective first jaw 172 and second jaw 174. The first channel 212 may be bound by side walls 216, 218 and a lower wall 220 of the first channel 212 (marked in FIG. 16). The second channel 214 may be bound by side walls 222, 224 and a lower wall 226 of the second channel 214 (marked in FIG. 16).

The first channel 212 may be curved in a plane 194 (marked in FIG. 14) that may be transverse or perpendicular to a plane of closure of the clip 170. The first channel 212 may curve towards a side direction that is transverse to the longitudinal extent of the first jaw 172. In examples, the curvature of the first channel 212 may match the curvature of the first side surface 178 or the second side surface 180 of the first jaw 172 (for example as shown in FIG. 13).

The second channel 214 may be curved in a plane 210 (marked in FIG. 14) that may be transverse or perpendicular to a plane of closure of the clip 170. The second channel 214 may curve towards a side direction that is transverse to the longitudinal extent of the second jaw 174. In examples, the curvature of the second channel 214 may match the curvature of the first side surface 196 or the second side surface 198 of the second jaw 174.

The curvature of the first channel 212 may match the curvature of the second channel 214 in examples.

Figures 18, 19, 20, 21:
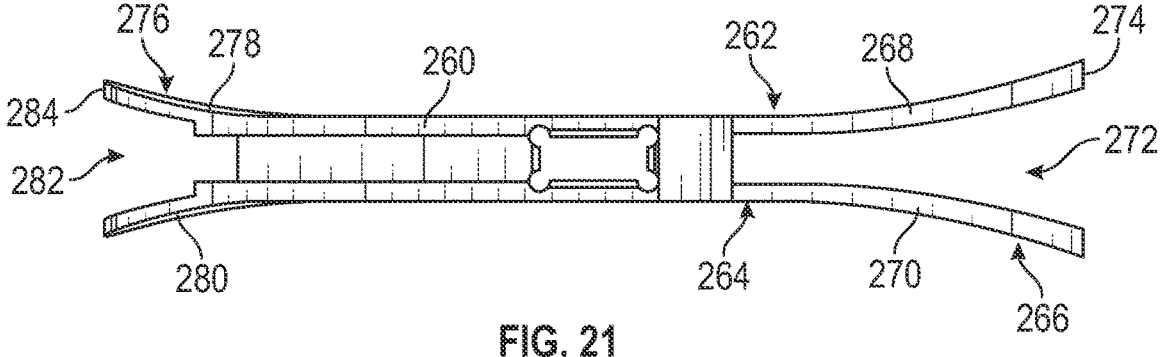
FIG. 18 illustrates a side view of a spring.
FIG. 19 illustrates a top view of the spring shown in FIG. 18.
FIG. 20 illustrates a perspective view of a first jaw of a clip.
FIG. 21 illustrates a top view of the first jaw shown in FIG. 20.

Referring to FIG. 18, the spring 176 may include a distal end portion 228 and a proximal end portion 230. The distal end portion 228 may include the ends 232, 234 of the spring 176 that may couple to respective central portions 173, 195 (marked in FIG. 12) of the first jaw 172 and the second jaw 174. The ends 232, 234 may couple to respective couplers 236, 238 (marked in FIG. 16) of the first jaw 172 and the second jaw 174. The proximal end portion 230 may include the loop 213 and curved portion 240 of the spring 176.

The spring 176 may include an outer surface 242 (marked in FIG. 19) and an inner surface 244 (marked in FIG. 18) facing opposite the outer surface 242. The inner surface 244 may face towards an opening 254 that the spring 176 surrounds. The spring 176 may further include a first side surface 246 (marked in FIG. 18) facing a first side direction and a second side surface 248 (marked in FIG. 19) facing a second side direction that is opposite the first side direction. The first side surface 246 and the second side surface 248 may each extend from the outer surface 242 to the inner surface 244.

The first side surface 246 may face a first side direction and may have a curvature. The first side surface 246 may be curved concave relative to the spring 176 in examples. The concave curvature may match a curvature of the first side surface 178 of the first jaw 172 or the first side surface 196 of the second jaw 174 in examples, or may have another curvature. The second side surface 248 may face a second side direction that is opposite the first side direction and may have a curvature. The second side surface 248 may be curved convex with respect to the spring 176 in examples. The convex curvature may match a curvature of the second side surface 180 of the first jaw 172 or the second side surface 198 of the second jaw 174 in examples, or may have another curvature.

The spring 176 may have a curvature in a plane that is transverse or perpendicular to a plane of closure of the clip 170. The spring 176 may curve towards a side direction that is transverse to the longitudinal extent of the clip 170.

In examples, the spring 176 may be curved to fit within the first channel 212 and the second channel 214 of the respective first jaw 172 and the second jaw 174. The curved spring 176 may extend within the curved channels 212, 214.

Referring to FIG. 18, the proximal end portion 230 of the spring 176 may have a height 250 in a plane of closure of the clip 170 that may be greater than a height 252 of the distal end portion 228 of the spring 176 in a plane of closure of the clip 170. As such, the spring 176 may be tapered downward in a direction from the proximal end portion 230 to the distal end portion 228 of the spring 176.

The spring 176 may be a C-shaped spring that may surround an opening 254 positioned interior of the inner surface 244 of the spring 176. The opening 254 may have a greater height or diameter 256 in a plane of closure of the clip 170 at the proximal end portion 230 of the spring 176 than a height or diameter 258 in a plane of closure of the clip 170 at the distal end portion 228 of the spring 176.

Figure 14:
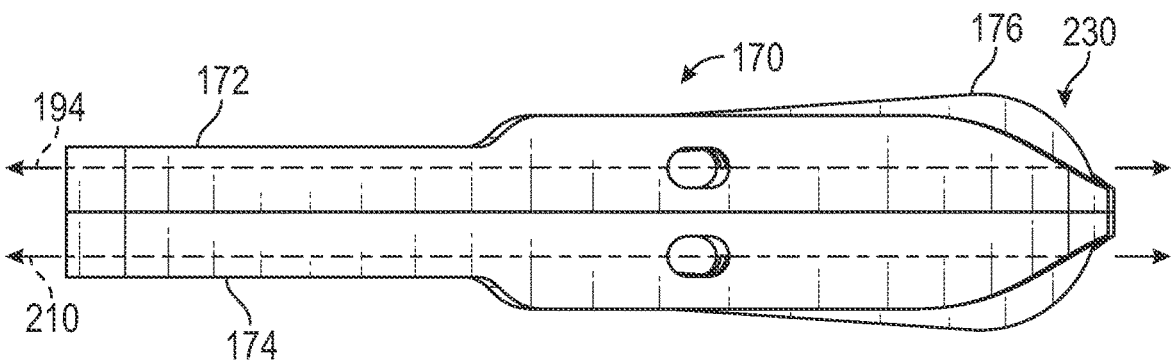
FIG. 14 illustrates a side view of the clip shown in FIG. 12.
Figure 16:
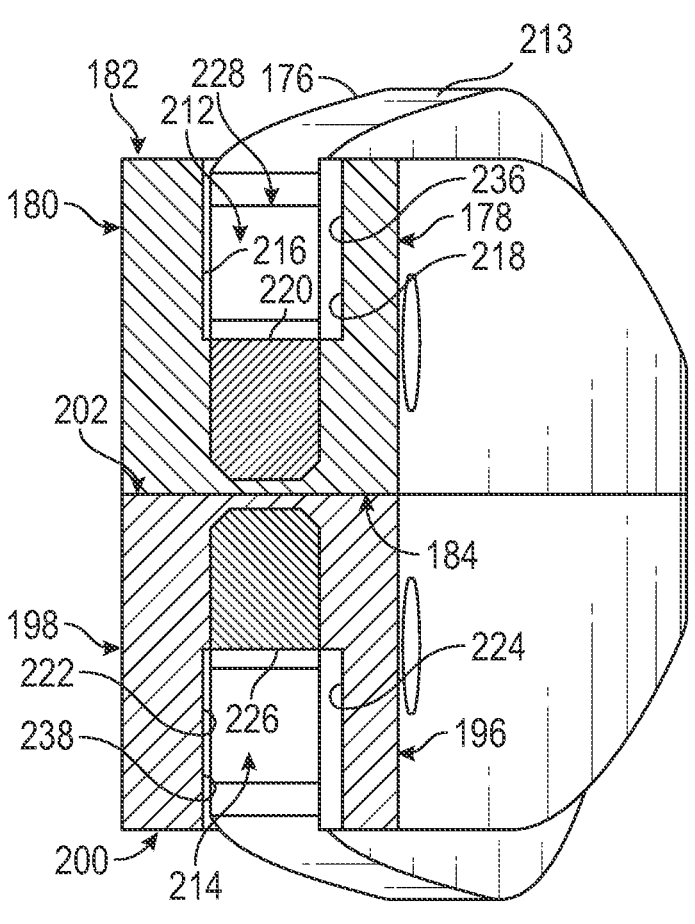
FIG. 16 illustrates a cross sectional view along line 16-16 in FIG. 13.

The tapered profile of the spring 176 may allow the distal end portion 228 of the spring 176 to be positioned at or within the outer surfaces 182, 200 of the respective first jaw 172 and second jaw 174 as shown in the cross sectional view of FIG. 16 (taken along line 16-16 in FIG. 13) and the side view of FIG. 14, for example. The respective outer surfaces 182, 200 of the first jaw 172 and the second jaw 174 may be at or raised above the distal end portion 228 of the spring 176.

Figure 17:
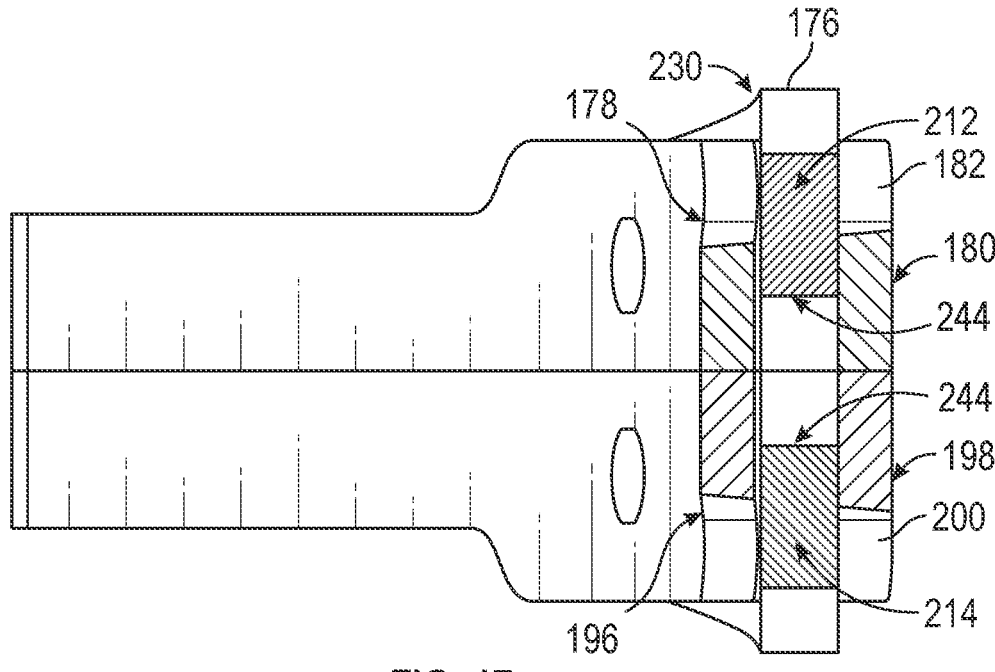
FIG. 17 illustrates a cross sectional view along line 17-17 in FIG. 13.

The proximal end portion 230 of the spring 176 may be raised above the outer surfaces 182, 200 of the respective first jaw 172 and second jaw 174 as shown in the cross sectional view of FIG. 17 (taken along line 17-17 in FIG. 13) and the side view of FIG. 14, for example.

Referring to FIG. 18, the tapered profile of the spring 176 and the increased height or diameter of the opening 254 at the proximal end portion 230 of the spring 176 may allow the clip 170 to open with the spring 176 forming a "U" shape to increase the amount of tissue that may be received between the jaws 172, 174. For example, the jaws 172, 174 may extend parallel with each other in a fully opened state, although other configurations may result.

Further, referring to FIG. 13, in examples, the proximal tip 186 of the first jaw 172 and second jaw 174 may be positioned at or protrude proximally from the proximal end portion 230 of the spring 176. The loop 213 of the spring 176 may extend proximally towards the second end portion 179 of the first jaw 172 and the second end portion 203 of the second jaw 174. The respective second end portions 179, 203 of the first jaw 172 and second jaw 174 may protrude proximally from or may be positioned at the loop 213. As such, a reduced possibility of tissue being pinned between the spring 176 and the proximal tip 186 at the fulcrum of the clip 170 may result.

The spring 176 may extend over the outer surface 182 of the first jaw 172 and the outer surface 200 of the second jaw 174 and may be configured to force the first jaw 172 and the second jaw 174 together to compress a portion of the heart between the compression surface 184 of the first jaw 172 and the compression surface 202 of the second jaw 174. The ends 232, 234 (marked in FIG. 18) of the spring 176 may be positioned such that the recess 181 shown in FIG. 12 is positioned between the first end 232 of the spring 176 and the second end portion 179 or proximal end portion of the first jaw 172. The recess 191 shown in FIG. 12 may be positioned between the second end 234 of the spring 176 and the second end portion 203 or proximal end portion of the second jaw 174.

Various other modifications of the clips disclosed herein may be provided. Various other methods of deployment and use of the clips may be provided as desired.

FIG. 20 illustrates a perspective view of a first jaw 260 of a clip 261 (shown in FIG. 22) that may be configured similarly as the clip 170 shown in FIGS. 12-17 unless stated otherwise. The first jaw 260 may include a first side surface 262 that may be curved concave with respect to the first jaw 260. The first jaw 260 may include a second side surface 264 facing opposite the first side surface 262 and that may be curved concave with respect to the first jaw 260. As such, the side surfaces 262, 264 may both be curved concave with respect to the first jaw 260 and may have opposite directions of curvature from each other.

A distal end portion 266 of the first jaw 260 may include a first side wall 268 and a second side wall 270 and a gap 272 between the first side wall 268 and the second side wall 270. The side walls 268, 270 may diverge from each other in a direction towards a distal tip 274 of the first jaw 260 such that a size of the gap 272 increases in a direction towards the distal tip 274. For example, FIG. 21 illustrates a triangular shaped gap 272 increasing in width in a direction towards the distal tip 274. The side walls 268, 270 may comprise flared distal ends of the first jaw 260.

In examples, the gap 272 may retain tissue between the side walls 268, 270 upon closure of the clip 261 to stabilize the position of the clip 261 upon deployment and reduce the possibility of movement of the clip 261 following deployment.

A proximal end portion 276 of the first jaw 260 may include a first side wall 278 and a second side wall 280 and a gap 282 between the first side wall 278 and the second side wall 280. The side walls 278, 280 may diverge from each other in a direction towards a proximal tip 284 of the first jaw 260 such that a size of the gap 282 increases in a direction towards the proximal tip 284. For example, FIG. 21 illustrates a triangular shaped gap 282 increasing in width in a direction towards the proximal tip 284. The side walls 278, 280 may comprise flared proximal ends of the first jaw 260.

In examples, the gap 282 may retain tissue between the side walls 278, 280 upon closure of the clip 261 to stabilize the position of the clip 261 upon deployment and reduce the possibility of movement of the clip 261 following deployment.

FIG. 21 illustrates a top view of the first jaw 260.

Figures 22, 23, 24:
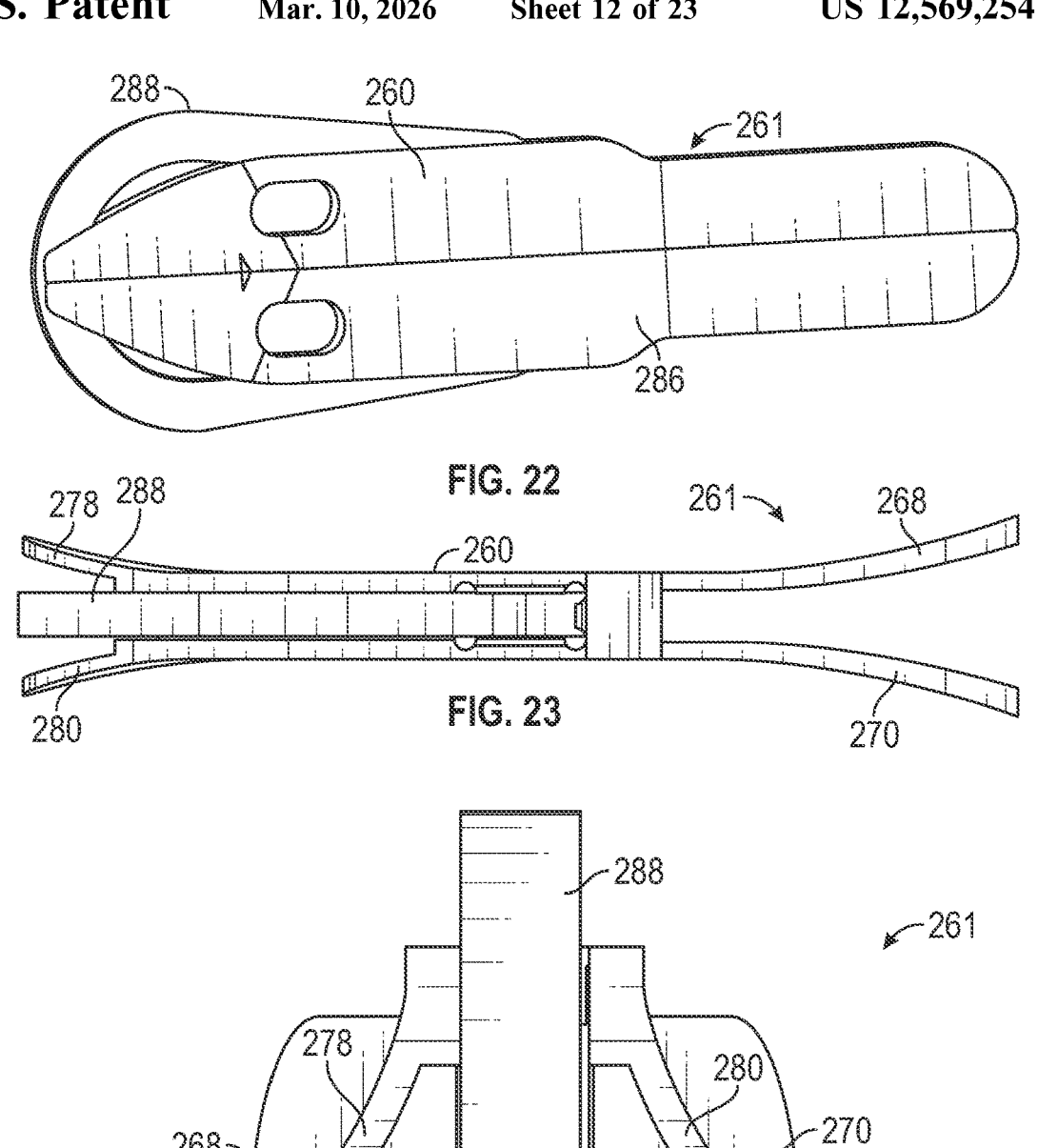
FIG. 22 illustrates a side view of a clip utilizing the first jaw shown in FIG. 20.
FIG. 23 illustrates a top view of the clip shown in FIG. 22.
FIG. 24 illustrates a proximal end view of the clip shown in FIG. 22.

Referring to FIG. 22, a second jaw 286 may be provided that may be configured similarly as the first jaw 260. The curvatures of the side surfaces of the second jaw 286, for example, may match the curvatures of the respective side surfaces 262, 264 of the first jaw 260.

The clip 261 may include a spring 288 that may compress the first jaw 260 towards the second jaw 286. The spring 288 may comprise a straight spring 288 that may lack a curvature in a side direction transverse to a plane of closure of the clip 261. For example, referring to FIG. 23, the spring 288 may be aligned with a longitudinal axis of the clip 261.

Figure 25:
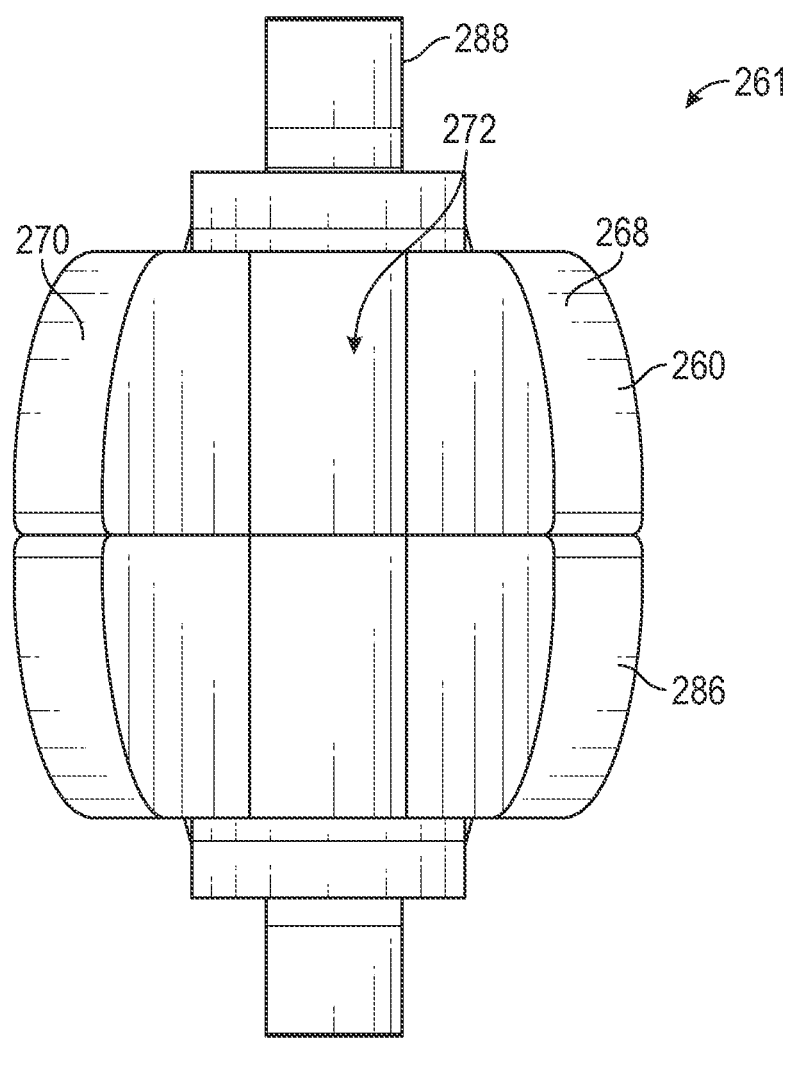
FIG. 25 illustrates a distal end view of the clip shown in FIG. 22.

FIG. 24 illustrates a proximal end view of the clip 261. FIG. 25 illustrates a distal end view of the clip 261.

Various other modifications of the clips disclosed herein may be provided. Various other methods of deployment and use of the clips may be provided as desired.

In examples, a cushion layer may be provided for one or more of a first jaw or a second jaw of a clip. The cushion layer may comprise the compression surface of one or more of the first jaw or the second jaw of a clip. A cushion layer may be provided on other components of a clip in examples (e.g., a spring). A cushion layer may have a variety of forms.

Figure 26:
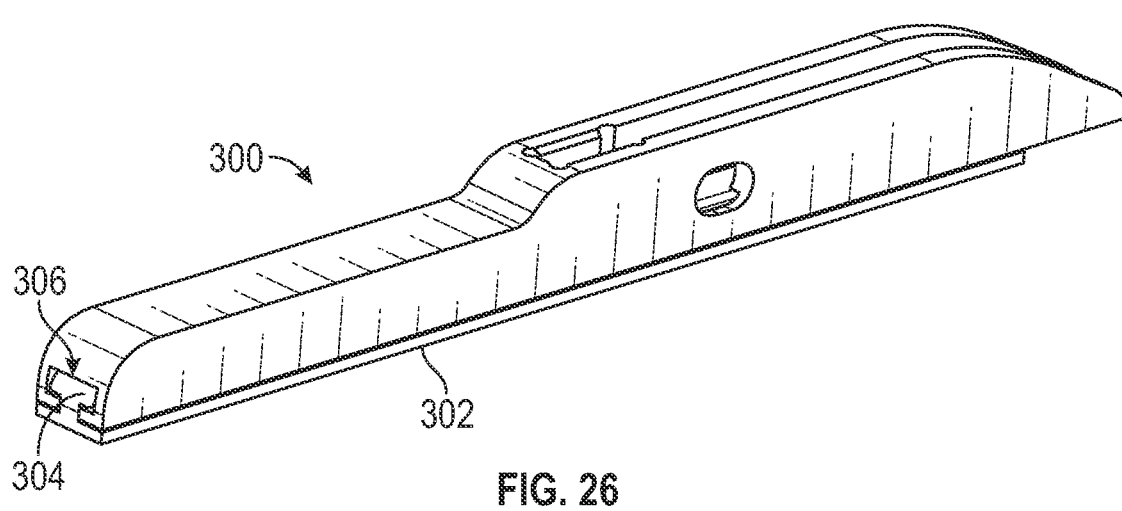
FIG. 26 illustrates a perspective view of a jaw.

For example, FIG. 26 illustrates a first jaw 300 that may be utilized in examples herein that may include a cushion layer 302 as the compression surface of the first jaw 300. The cushion layer 302 may comprise an elongate strip of material that may include an engagement portion 304 configured to slide into a receiving portion 306 of the first jaw 300. The engagement portion 304 may comprise a dovetail protrusion. The receiving portion 306 may comprise an elongate track configured to receive the dovetail protrusion and may extend along the length of the first jaw 300. The engagement portion 304 may slide into the receiving portion 306.

Figure 27:
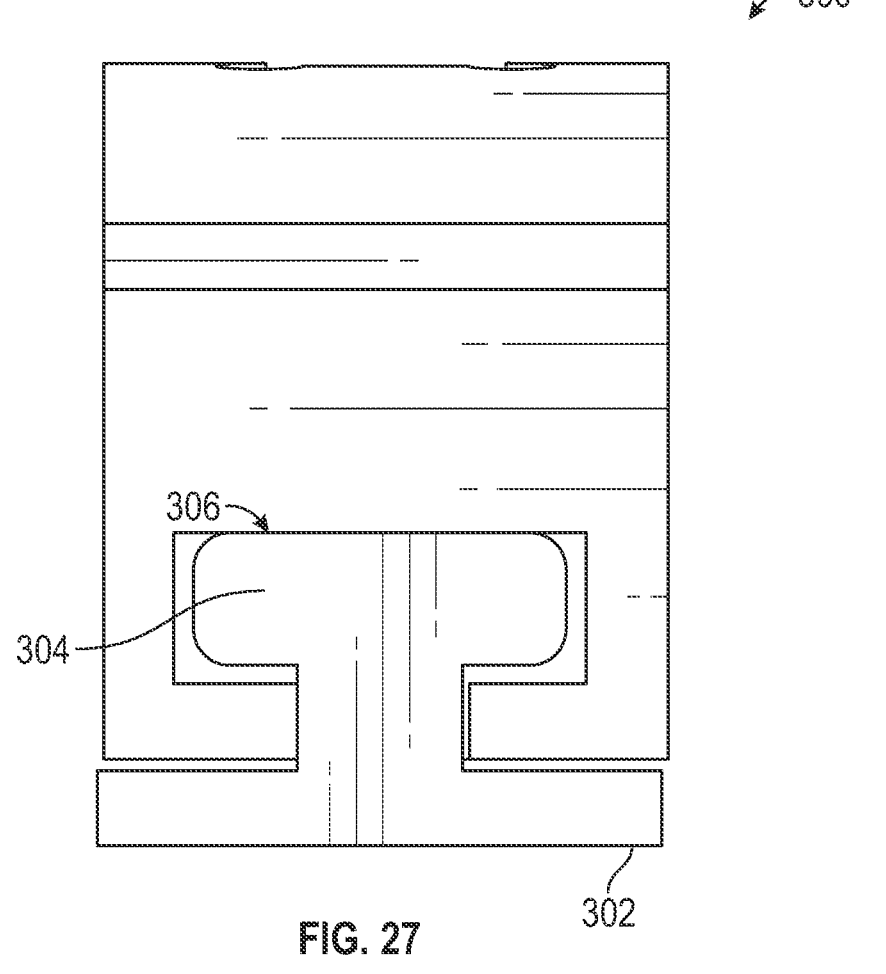
FIG. 27 illustrates a distal end view of the jaw shown in FIG. 26.
Figures 28, 29:
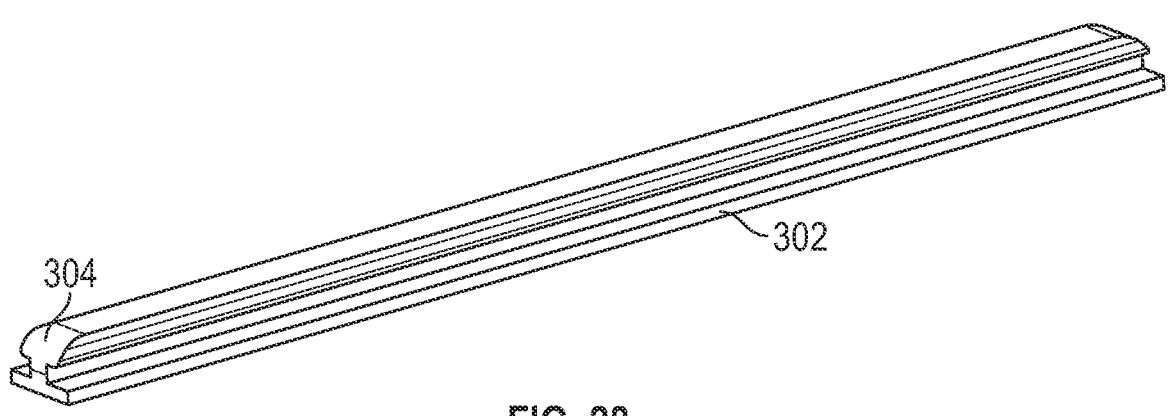
FIG. 28 illustrates a perspective view of a cushion layer.
FIG. 29 illustrates a perspective view of a jaw.

FIG. 27, for example, illustrates an end view of the first jaw 300 showing the engagement portion 304 received into the receiving portion 306 in the form of a track. FIG. 28 illustrates a perspective view of the cushion layer 302 separate from the body of the first jaw 300.

In assembly, the cushion layer 302 may be molded or otherwise separately formed and then slid into the receiving portion 306 to retain the cushion layer 302 to the body of the first jaw 300.

In examples, the cushion layer 302 may comprise a compliant material that may be configured to deflect upon compression with the portion of the heart being compressed. The compliant material may comprise an elastomeric material such as a silicone or rubber or other form of elastomeric material. The compliant material may be formed separate from the body of the first jaw 300 and then engaged with the body of the first jaw 300.

The cushion layer may have a variety of configurations in examples. For example, FIG. 29 illustrates a configuration of a cushion layer 308 having an elongate channel 310. The elongate channel 310 may comprise an interior cavity extending along the length of the elongate cushion layer 308. FIG. 30, for example, illustrates an end view of the cushion layer 308. The receiving portion 306 may comprise an elongate track, similar to the receiving portion 306 shown in FIG. 26. FIG. 31 illustrates a perspective view of the cushion layer 308.

In examples, one or more of a first jaw or a second jaw may include a cushion layer. FIG. 32, for example, illustrates a second jaw 312 including a cushion layer 314. The cushion layer 314 may have a similar configuration as the cushion layer 308. In examples, a cushion layer of a second jaw 312 may have a different configuration than a cushion layer of a first jaw 300.

Figure 33:
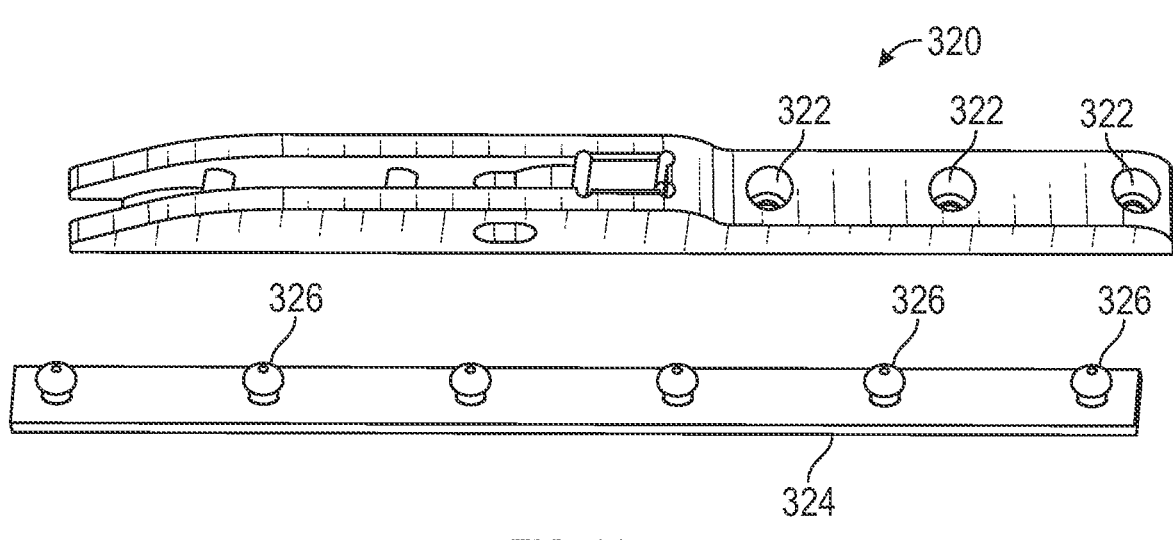
FIG. 33 illustrates an assembly view of a jaw.

In examples, a cushion layer may couple to a jaw in a variety of other manners. FIG. 33, for example, illustrates a first jaw 320 including a receiving portion 322 comprising a plurality of apertures for receiving the cushion layer 324. The cushion layer 324 may include an engagement portion 326 comprising a plurality of pins configured to insert into the plurality of apertures to couple with the first jaw 320.

Figure 34:
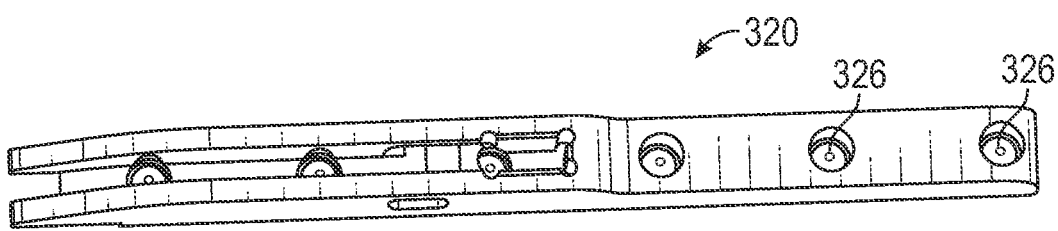
FIG. 34 illustrates a perspective view of the jaw shown in FIG. 33.
Figure 35:
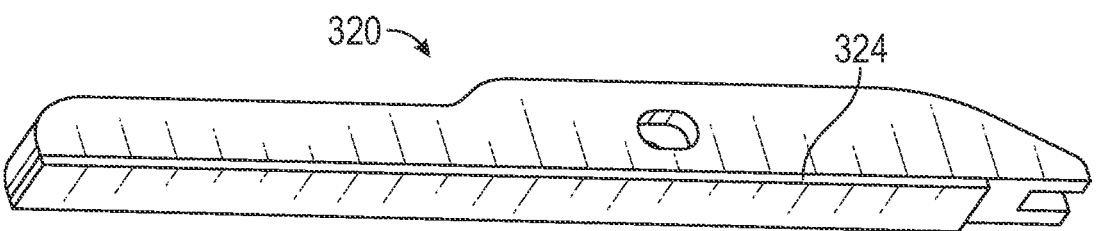
FIG. 35 illustrates a lower perspective view of the jaw shown in FIG. 34.

FIG. 34, for example, illustrates the cushion layer 324 engaged with the first jaw 320. FIG. 35 illustrates a lower perspective view of the first jaw 320 showing the configuration of the cushion layer 324 as the compression surface of the first jaw 320.

The cushion layer 324 may be formed or molded separately from the first jaw 320 and may be inserted into the apertures of the first jaw 320.

In examples, a cushion layer may couple to a jaw in a variety of other manners.

Figure 36:
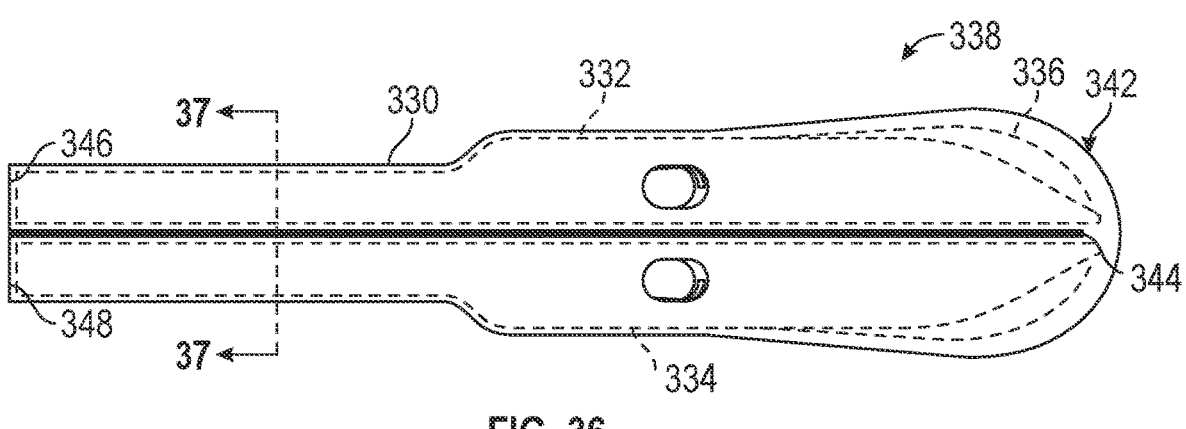
FIG. 36 illustrates a side view of a clip.
Figure 37:
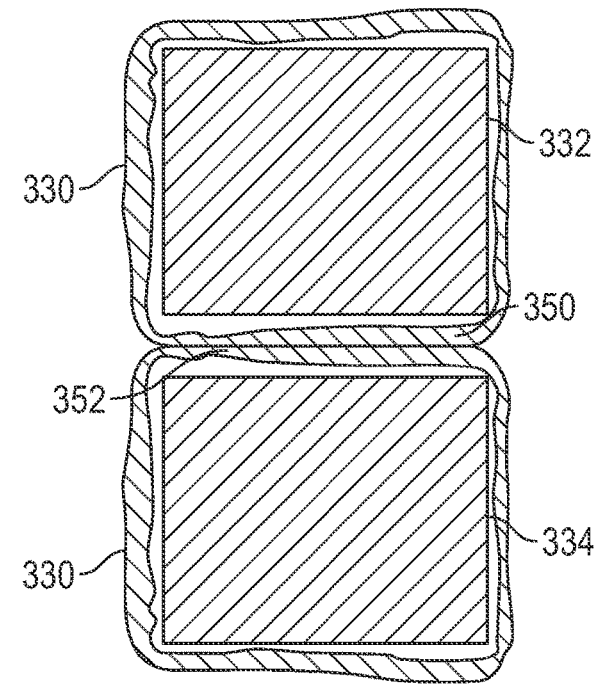
FIG. 37 illustrates a cross sectional view along line 37-37 in FIG. 36.

In examples, a cushion layer may comprise one or more sleeves covering one or more of a first jaw or a second jaw, or another portion of a clip. FIGS. 36 and 37, for example, illustrate an example in which a cushion layer comprises a single sleeve 330 configured to cover a first jaw 332, a second jaw 334, and a spring 336 of a clip 338. The sleeve 330 may comprise a single elongate tube that may extend over the first jaw 332 and may curve around the proximal end portion 342 of the clip 338 to cover the second jaw 334. A crease 344 of the sleeve 330 may be positioned at the proximal end portion 342 of the clip 338 where the sleeve 330 extends around the first jaw 332 to the second jaw 334 at the fulcrum of the clip 338. The one or more sleeves may comprise a compliant material that may be configured to deflect upon compression with the portion of the heart being compressed. The compliant material may comprise an elastomeric material such as a silicone or rubber or other form of elastomeric material. The one or more sleeves may comprise polytetrafluoroethylene (PTFE). Expanded PTFE (ePTFE) may be utilized in examples.

The ends 346, 348 of the sleeve 330 may be closed in a variety of manners. In examples, adhesives or heating of the ends 346, 348 may be utilized to close the ends 346, 348, among other methods.

FIG. 37 illustrates a cross sectional view of the clip 338 along line 37-37 in FIG. 36. The sleeve 330 is shown to cover the first jaw 332 and the second jaw 334 and form a cushion layer 350 of the first jaw 332 and a cushion layer 352 of the second jaw 334. The cushion layer 350 may comprise the compression surface of the first jaw 332. The cushion layer 352 may comprise the compression surface of the second jaw 334.

Various configurations of cushion layers may be provided in examples.

Figure 38:
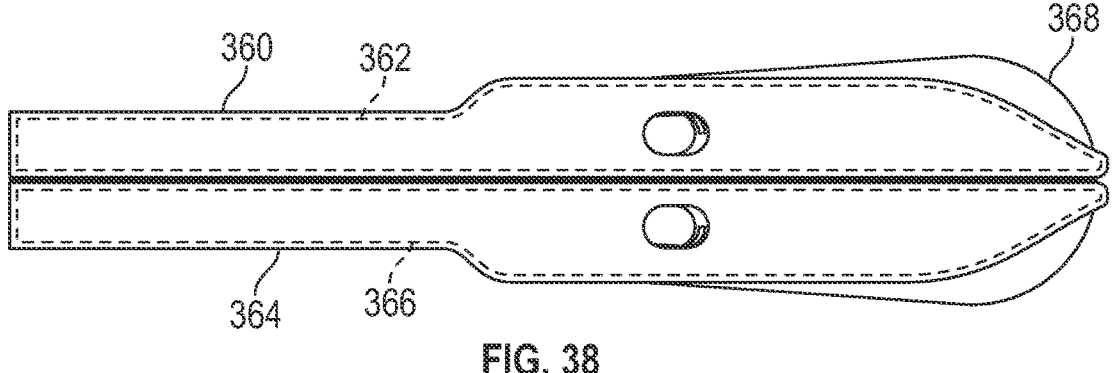
FIG. 38 illustrates a side view of a clip.

FIG. 38 illustrates an example in which a first sleeve 360 may cover a first jaw 362 and a second sleeve 364 may cover a second jaw 366. Separate sleeves accordingly may be utilized for the first jaw 362 and the second jaw 366. In examples, the spring 368 may remain uncovered by a sleeve. In examples, one or more sleeves (e.g., a third sleeve) may cover the spring 368.

Figure 39:
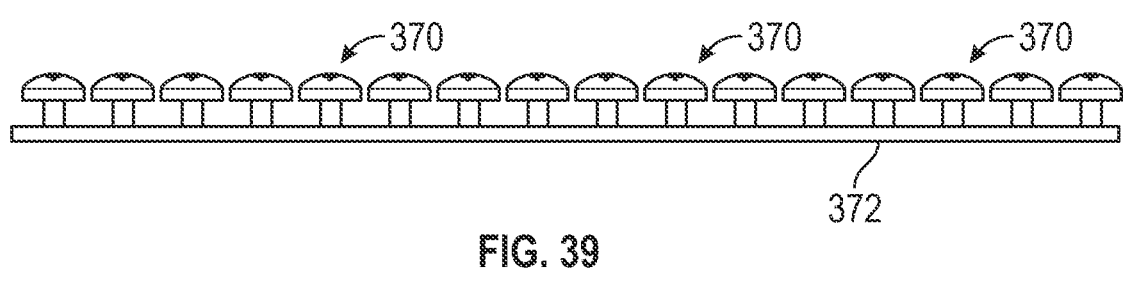
FIG. 39 illustrates a side view of a strip of plugs.
Figure 40:
FIG. 40 illustrates a side view of a plug.

In examples, ends of a sleeve may be coupled to a first jaw or second jaw through use of a coupler. FIG. 39, for example, illustrates a formed string of couplers comprising plugs 370. A plug 370 may be removed from a strip 372 of plugs 370. FIG. 40, for example, illustrates a plug 370 including an insertion portion 374 or stem and a relatively wider head 376. The plug 370 may be utilized to couple to ends of one or more sleeves to couple to one or more of the jaws.

One or more plugs may be positioned at a first end portion or distal end portion of a first jaw or second jaw and may be coupled to one or more sleeves.

Figure 41:
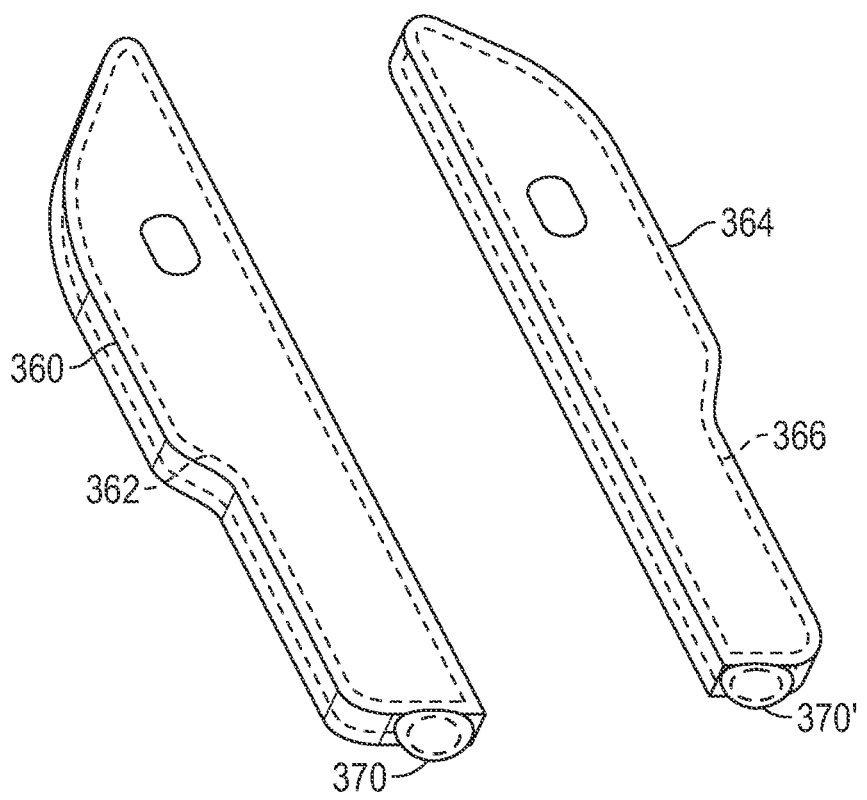
FIG. 41 illustrates a perspective view of a first jaw and a second jaw.

FIG. 41, for example, illustrates a first plug 370 utilized to couple an end of a sleeve 360 to an end of a first jaw 362. Similarly, a second plug 370' may be utilized to couple an end of a sleeve 364 to an end of a second jaw 366. One or more plugs may be utilized with ends of a single sleeve (as shown in FIG. 36 for example), or ends of multiple sleeves (in a configuration as shown in FIG. 38 for example).

The plugs 370 may be inserted into jaws 362, 366 with insertion portions 374 of plugs 370 inserted into the jaws 362, 366. The relatively wider heads 376 may overlap a portion of ends of sleeves to couple to the jaws 362, 366.

Further, the heads 376 of the plugs 370 may have a smooth surface to be atraumatic to the tissue of an individual's body upon insertion into the individual's body.

In examples, an adhesive may be provided to secure the plugs in position if desired.

Figures 42, 43, 44, 45:
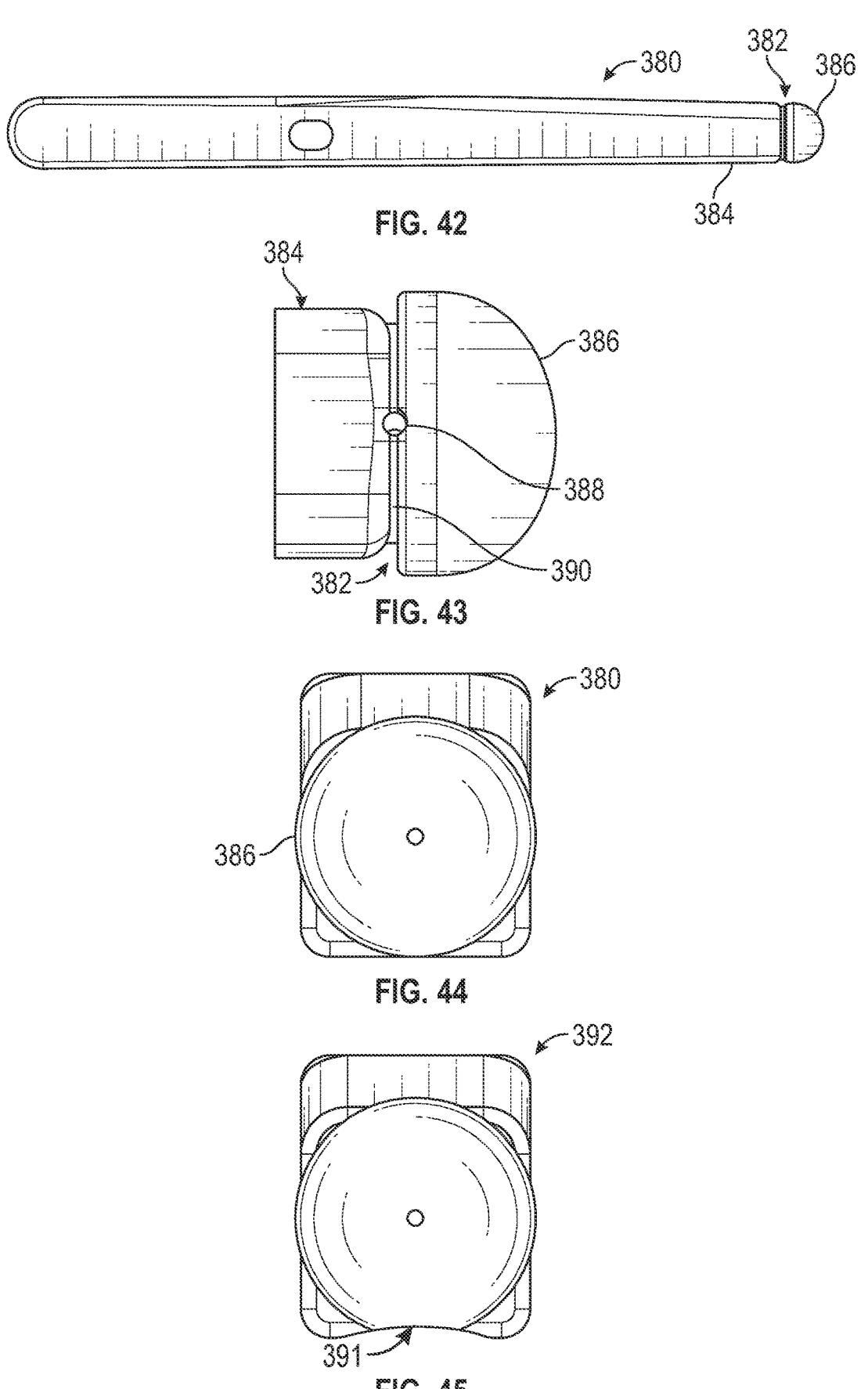
FIG. 42 illustrates a side view of a jaw.
FIG. 43 illustrates a close up view of a distal end portion of a jaw.
FIG. 44 illustrates an end view of the jaw shown in FIG. 42.
FIG. 45 illustrates an end view of a jaw.

In examples, other forms of coupling to a jaw may be provided. FIG. 42, for example, illustrates an example of a jaw 380 including a suture receiving portion 382 at a distal end portion 384 of the jaw 380. The suture receiving portion 382 may comprise a channel that extends circumferentially about the jaw 380.

FIG. 43, for example, illustrates a close up view of the distal end portion 384 of the jaw 380. The suture receiving portion 382 is shown positioned proximal of the distal tip 386. The suture receiving portion 382 may include an aperture 388 that a suture may be passed through and then wrapped about the channel 390.

FIG. 44 illustrates an end view of the first jaw 380.

Referring to FIG. 45, in examples, a compressive surface 391 of a first jaw 392 may be curved about an axis extending parallel with a longitudinal axis of the first jaw 392. Such curvature may enhance the conformability of the jaw to the portion of the heart being occluded.

Figures 46, 47, 48:
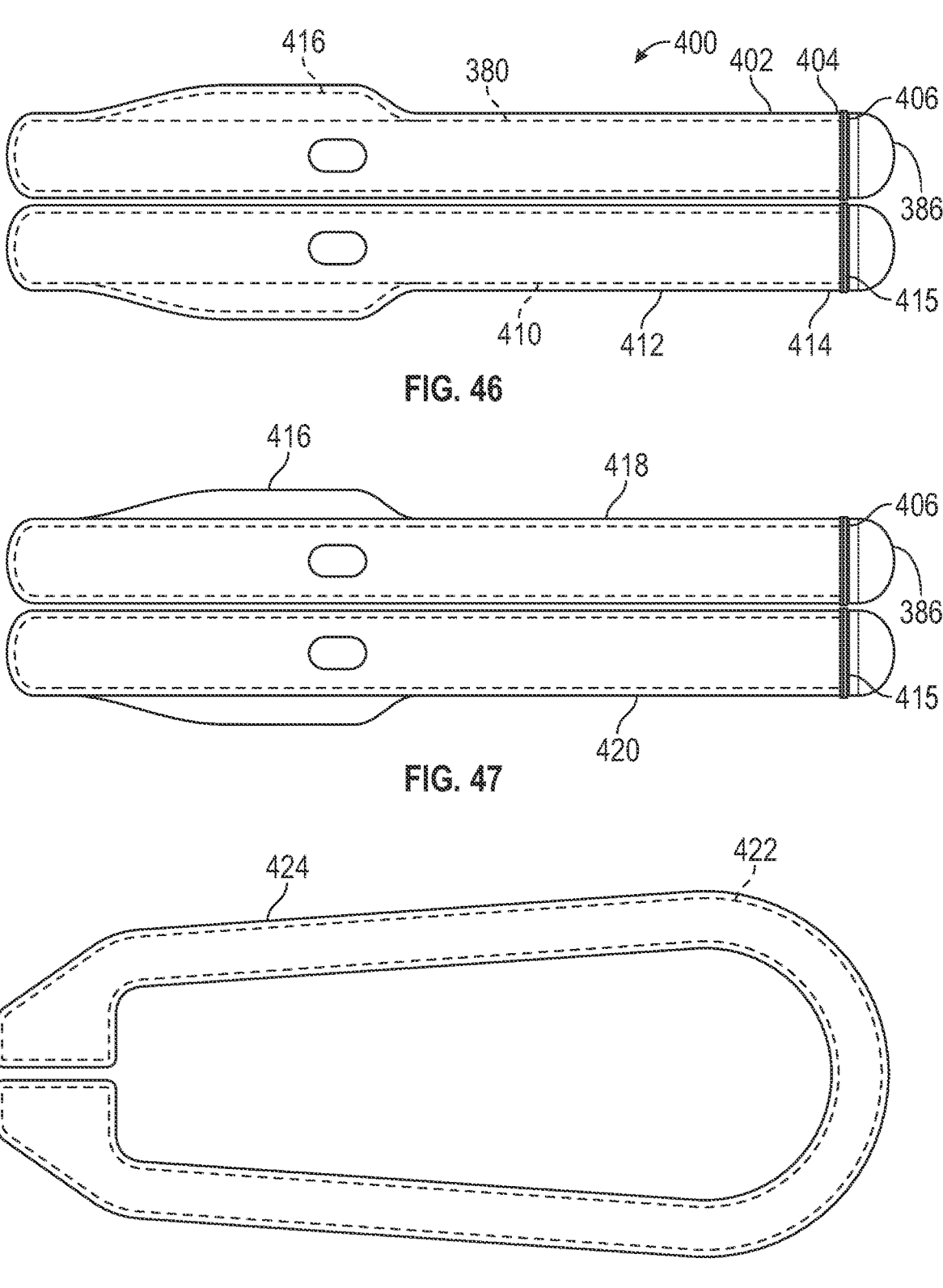
FIG. 46 illustrates a side view of a clip.
FIG. 47 illustrates a side view of a clip.
FIG. 48 illustrates a side view of a spring.

FIG. 46 illustrates a configuration of a clip 400 utilizing the first jaw 380. A sleeve 402 may extend over the first jaw 380 and may have a distal end 404 that sutures 406 may extend over. One or more sutures 406 may be positioned at a first end portion of the first jaw 380 and may be coupled to one or more of the sleeves. The sutures 406 may couple the distal end 404 of the sleeve 402 to the first jaw 380.

The clip 400 may similarly include a second jaw 410. A sleeve 412 may extend over the second jaw 410 and may have a distal end 414 that sutures 415 may extend over. The sutures 415 may couple the distal end 414 of the sleeve 412 to the second jaw 410.

In examples, an adhesive may be provided over the sutures if desired.

In the example of FIG. 46, one or more of the sleeves 402, 412 may extend over a spring 416 for the clip 400. In examples, a single sleeve may extend over the first jaw 380 and the second jaw 410 and the spring 416. In an example as shown in FIG. 47, the spring 416 may be uncovered by the sleeves 418, 420.

In examples, a spring may be wrapped with a cushion layer. For example, referring to FIG. 48, a spring 422 may be wrapped with a layer of cushion material 424 such as polytetrafluoroethylene (PTFE). A PTFE tape may be wrapped around the spring 422. Expanded PTFE (ePTFE) may be utilized in examples. Other forms of cushion material 424 may be utilized in examples.

Figure 49:
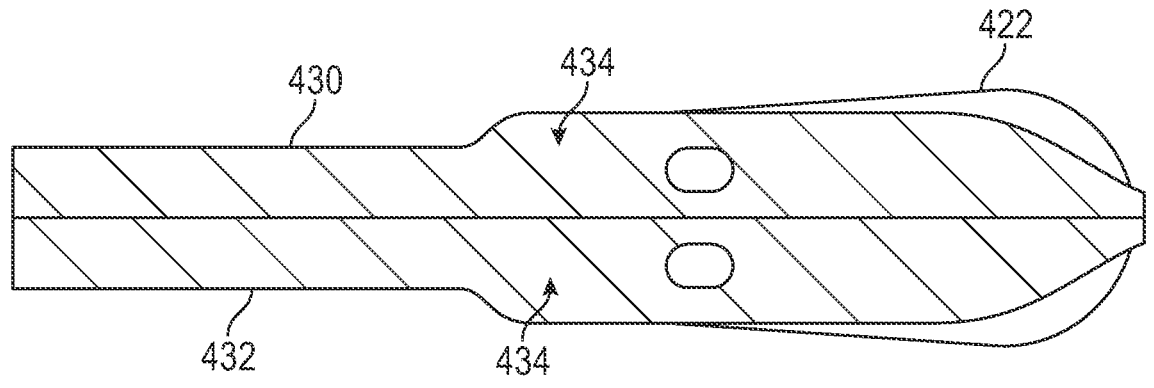
FIG. 49 illustrates a side view of a clip.

In examples, one or more of a first jaw or second jaw may be wrapped with a layer of cushion material. FIG. 49, for example, illustrates a first jaw 430 and a second jaw 432 each wrapped with a layer of cushion material 434 comprising polytetrafluoroethylene (PTFE). A PTFE tape may be wrapped around the first jaw 430 or second jaw 432. Expanded PTFE (ePTFE) may be utilized in examples. Other forms of cushion material 434 may be utilized in examples. The spring 422 may be wrapped with a same cushion material as the first jaw 430 or the second jaw 432 or may have another form in examples.

Figure 50:
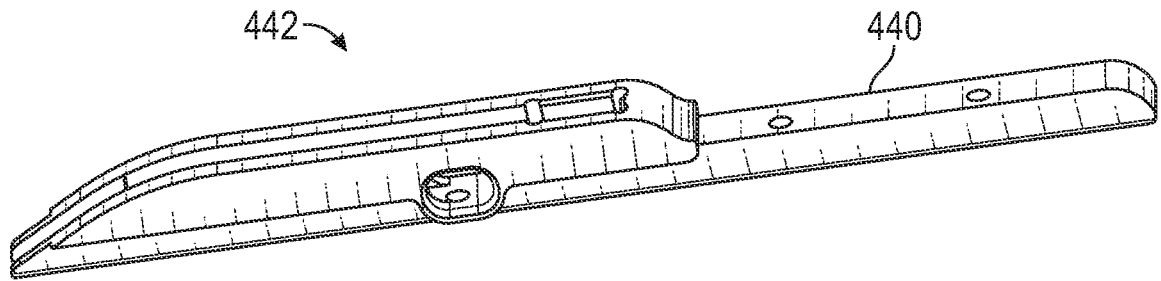
FIG. 50 illustrates a perspective view of a portion of a jaw.
Figure 51:
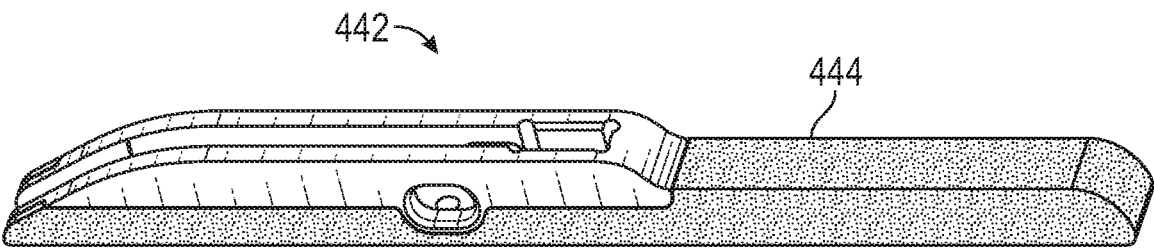
FIG. 51 illustrates a perspective view of a jaw.

In examples, a layer of cushion material may be overmolded upon a portion of a first jaw or a second jaw. FIG. 50, for example illustrates a first portion 440 of a first jaw 442 that may be formed by molding or another process. Referring to FIG. 51, an overmolding 444 of cushion material may be provided upon the first portion 440 to form a cushion layer for the first jaw 442. The compression surface of the first jaw 442 may include the overmolding 444. A second jaw may be formed in a similar manner.

A cushion layer may comprise a medical grade soft material that may make the compression surfaces of the jaws atraumatic if desired. The cushion layer may comprise an elastomeric material, such as silicone, rubber, or another form of material that may deform upon an applied pressure. PTFE or ePTFE (e.g., PTFE or ePTFE tubes) may be utilized as desired. Other configurations of cushion layers may be provided on other portions of clips as desired. The body of the jaw may comprise a relatively rigid plastic such as polyetheretherketone (PEEK), or may be made of another material (e.g., a metal or more compliant material). The spring may be made of a shape memory material such as nitinol or may be made of another material (e.g., stainless steel or cobalt chromium, among others). Features disclosed in regard to the cushion layers may be utilized in any example of clip disclosed herein.

The clips disclosed in regard to FIGS. 12-51 may be deployed and utilized in a similar manner as the clips disclosed in regard to FIGS. 2-11, or in another manner as desired. Repositioning or redeployment may occur in a similar manner as the clips disclosed in regard to FIGS. 2-11, or in another manner as desired.

Various other modifications of the clips disclosed herein may be provided. Various other methods of deployment and use of the clips may be provided as desired.

The clips as disclosed herein may be utilized to close the LAA or may be utilized to close another portion of a heart. In examples, the clips may be utilized to close other portions of a body, including other tubular vessels or other portions of a body. Deployment may be via a delivery apparatus or via another method as desired. Deployment may be via surgical methods and may be transcatheter or via non-invasive surgery in methods.

Variations in the clips and methods disclosed herein may be provided. Features across examples may be combined. Features may be excluded or added to in various examples disclosed herein. Combinations of features of examples may be provided. The clips may be utilized solely or in methods disclosed herein, or in combination with other devices disclosed herein.

For purposes of this description, certain aspects, advantages, and novel features of the examples of this disclosure are described herein. The disclosed methods, apparatuses, and systems should not be construed as limiting in any way. Instead, the present disclosure is directed toward all novel and nonobvious features and aspects of the various disclosed examples, alone and in various combinations and sub-combinations with one another. The methods, apparatuses, and systems are not limited to any specific aspect or feature or combination thereof, nor do the disclosed examples require that any one or more specific advantages be present or problems be solved. Features, elements, or components of one example can be combined into other examples herein.

Example 1: A clip for a portion of a heart, the clip comprising: a first jaw extending from a first end portion to a second end portion and including a compression surface and an outer surface facing opposite the compression surface; a second jaw extending from a first end portion to a second end portion and including a compression surface facing the compression surface of the first jaw and an outer surface facing opposite the compression surface of the second jaw; and a spring extending over the outer surface of the first jaw and the outer surface of the second jaw and configured to force the first jaw and the second jaw together to compress the portion of the heart between the compression surface of the first jaw and the compression surface of the second jaw.

Example 2: The clip of any example herein, in particular Example 1, wherein: the first jaw includes a central portion between the first end portion and the second end portion of the first jaw; the second jaw includes a central portion between the first end portion and the second end portion of the second jaw; and the spring includes a first end coupled to the central portion of the first jaw and a second end coupled to the central portion of the second jaw.

Example 3: The clip of any example herein, in particular Example 2, wherein the spring includes a loop extending towards the second end portion of the first jaw and the second end portion of the second jaw.

Example 4: The clip of any example herein, in particular Example 3, wherein: the outer surface of the first jaw includes a channel; the outer surface of the second jaw includes a channel; and the loop extends within the channel of the first jaw and the channel of the second jaw.

Example 5: The clip of any example herein, in particular Example 3 or Example 4, wherein the loop protrudes from the second end portion of the first jaw and the second end portion of the second jaw.

Example 6: The clip of any example herein, in particular Examples 1-5, wherein the first end portion of the first jaw is tapered, and the second end portion of the first jaw is tapered.

Example 7: The clip of any example herein, in particular Examples 1-6, wherein the first jaw includes a side surface extending from the compression surface to the outer surface of the first jaw, and the side surface includes a recess for receiving a device for applying an expansion force to the spring.

Example 8: The clip of any example herein, in particular Example 7, wherein the recess is positioned between a first end of the spring and the second end portion of the first jaw.

Example 9: The clip of any example herein, in particular Example 7 or Example 8, wherein the second jaw includes a side surface extending from the compression surface to the outer surface of the second jaw, and the side surface includes a recess for receiving the device for applying the expansion force to the spring.

Example 10: The clip of any example herein, in particular Examples 1-9, wherein the spring includes a recess for receiving a device for applying an expansion force to the spring.

Example 11: The clip of any example herein, in particular Examples 1-10, wherein: the spring includes a loop extending proximally towards the second end portion of the first jaw and the second end portion of the second jaw; the second end portion of the first jaw protrudes proximally from or is positioned at the loop; and the second end portion of the second jaw protrudes proximally from or is positioned at the loop.

Example 12: The clip of any example herein, in particular Examples 1-11, wherein: the first jaw includes a side surface extending from the compression surface to the outer surface of the first jaw, and the side surface is curved concave relative to the first jaw; and the second jaw includes a side surface extending from the compression surface to the outer surface of the second jaw, and the side surface of the second jaw is curved concave relative to the second jaw.

Example 13: The clip of any example herein, in particular Example 12, wherein: the side surface of the first jaw comprises a first side surface facing a first side direction, and the first jaw includes a second side surface facing opposite the first side surface and being curved convex relative to the first jaw; and the side surface of the second jaw comprises a third side surface facing the first side direction, and the second jaw includes a fourth side surface facing opposite the third side surface and being curved convex relative to the second jaw.

Example 14: The clip of any example herein, in particular Example 12, wherein: the side surface of the first jaw comprises a first side surface facing a first side direction, and the first jaw includes a second side surface facing opposite the first side surface and being curved concave relative to the first jaw; and the side surface of the second jaw comprises a third side surface facing the first side direction, and the second jaw includes a fourth side surface facing opposite the third side surface and being curved concave relative to the second jaw.

Example 15: The clip of any example herein, in particular Examples 12-14, wherein the side surface of the first jaw has a constant curvature, and the side surface of the second jaw has a constant curvature.

Example 16: The clip of any example herein, in particular Examples 12-15, wherein the side surface of the first jaw is curved concave relative to the first jaw from a proximal tip of the first jaw to a distal tip of the first jaw.

Example 17: The clip of any example herein, in particular Examples 1-16, wherein the spring has an outer surface, an inner surface, a first side surface extending from the outer surface to the inner surface and facing a first side direction, and a second side surface extending from the outer surface to the inner surface and facing a second side direction that is opposite the first side direction, and the first side surface is curved concave relative to the spring.

Example 18: The clip of any example herein, in particular Example 17, wherein the second side surface is curved convex relative to the spring.

Example 19: The clip of any example herein, in particular Examples 1-18, wherein: the outer surface of the first jaw includes a channel that is curved in a plane transverse to a plane of closure of the clip; the outer surface of the second jaw includes a channel that is curved in a plane transverse to the plane of closure of the clip; and the spring is curved in a plane transverse to the plane of closure of the clip and extends within the channel of the first jaw and the channel of the second jaw.

Example 20: The clip of any example herein, in particular Examples 1-19, wherein the spring includes: a distal end portion having a height in a plane of closure of the clip and including a first end coupled to the first jaw and a second end coupled to the second jaw; and a proximal end portion having a height in the plane of closure of the clip and including a loop extending towards the second end portion of the first jaw and the second end portion of the second jaw, and wherein the height of the proximal end portion of the spring is greater than the height of the distal end portion of the spring.

Example 21: The clip of any example herein, in particular Example 20, wherein the spring comprises a C-shaped spring surrounding an opening, and wherein a diameter of the opening at the proximal end portion of the spring is greater than a diameter of the opening at the distal end portion of the spring.

Example 22: The clip of any example herein, in particular Example 20 or Example 21, wherein the proximal end portion of the spring is raised above the outer surface of the first jaw and is raised above the outer surface of the second jaw.

Example 23: The clip of any example herein, in particular Examples 20-22, wherein the outer surface of the first jaw is at or is raised above the distal end portion of the spring, and the outer surface of the second jaw is at or is raised above the distal end portion of the spring.

Example 24: The clip of any example herein, in particular Examples 1-23, wherein the second end portion of the first jaw is tapered, and the second end portion of the second jaw is tapered.

Example 25: The clip of any example herein, in particular Examples 1-24, wherein the first end portion of the first jaw includes a distal tip and a first side wall and a second side wall and a gap between the first side wall and the second side wall, and the first side wall and the second side wall diverge away from each other in a direction towards the distal tip.

Example 26: The clip of any example herein, in particular Example 25, wherein a width of the gap increases in a direction towards the distal tip.

Example 27: The clip of any example herein, in particular Examples 1-26, wherein the second end portion of the first jaw includes a proximal tip and a first side wall and a second side wall and a gap between the first side wall and the second side wall, and the first side wall and the second side wall diverge away from each other in a direction towards the proximal tip.

Example 28: The clip of any example herein, in particular Example 27, wherein a width of the gap increases in a direction towards the proximal tip.

Example 29: The clip of any example herein, in particular Examples 1-28, wherein the compression surface of the first jaw includes a cushion layer.

Example 30: The clip of any example herein, in particular Example 29, wherein the cushion layer is received within a track of the first jaw.

Example 31: The clip of any example herein, in particular Example 29 or Example 30, wherein the first jaw includes one or more apertures for receiving the cushion layer.

Example 32: The clip of any example herein, in particular Examples 29-31, wherein the cushion layer includes an elongate channel extending along the cushion layer.

Example 33: The clip of any example herein, in particular Examples 29-32, wherein the cushion layer comprises an overmolding upon a portion of the first jaw.

Example 34: The clip of any example herein, in particular Examples 1-33, further comprising one or more sleeves covering the first jaw and the second jaw.

Example 35: The clip of any example herein, in particular Example 34, wherein a single sleeve covers the first jaw and the second jaw.

Example 36: The clip of any example herein, in particular Example 34, wherein a first sleeve covers the first jaw and a second sleeve covers the second jaw.

Example 37: The clip of any example herein, in particular Examples 34-36, wherein the one or more sleeves cover the spring.

Example 38: The clip of any example herein, in particular Examples 34-37, further comprising one or more plugs positioned at the first end portion of the first jaw and coupled to the one or more sleeves.

Example 39: The clip of any example herein, in particular Examples 34-38, further comprising one or more sutures positioned at the first end portion of the first jaw and coupled to the one or more sleeves.

Example 40: The clip of any example herein, in particular Examples 1-39, wherein the clip is configured to occlude a left atrial appendage.

Example 41: A method comprising: deploying a clip to close a portion of a heart, the clip including: a first jaw extending from a first end portion to a second end portion and including a compression surface and an outer surface facing opposite the compression surface, a second jaw extending from a first end portion to a second end portion and including a compression surface facing the compression surface of the first jaw and an outer surface facing opposite the compression surface of the second jaw, and a spring extending over the outer surface of the first jaw and the outer surface of the second jaw and configured to force the first jaw and the second jaw together to compress the portion of the heart between the compression surface of the first jaw and the compression surface of the second jaw.

Example 42: The method of any example herein, in particular Example 41, wherein the portion of the heart is a left atrial appendage.

Example 43: The method of any example herein, in particular Example 41 or Example 42, wherein: the first jaw includes a central portion between the first end portion and the second end portion of the first jaw, the second jaw includes a central portion between the first end portion and the second end portion of the second jaw, and the spring includes a first end coupled to the central portion of the first jaw and a second end coupled to the central portion of the second jaw.

Example 44: The method of any example herein, in particular Example 43, wherein the spring includes a loop extending towards the second end portion of the first jaw and the second end portion of the second jaw.

Example 45: The method of any example herein, in particular Example 44, wherein: the outer surface of the first jaw includes a channel, the outer surface of the second jaw includes a channel, and the loop extends within the channel of the first jaw and the channel of the second jaw.

Example 46: The method of any example herein, in particular Example 44 or Example 45, wherein the loop protrudes from the second end portion of the first jaw and the second end portion of the second jaw.

Example 47: The method of any example herein, in particular Examples 41-46, wherein the first end portion of the first jaw is tapered, and the second end portion of the first jaw is tapered.

Example 48: The method of any example herein, in particular Examples 41-47, wherein the first jaw includes a side surface extending from the compression surface to the outer surface of the first jaw, and the side surface includes a recess for receiving a device for applying an expansion force to the spring.

Example 49: The method of any example herein, in particular Example 48, wherein the recess is positioned between a first end of the spring and the second end portion of the first jaw.

Example 50: The method of any example herein, in particular Example 48 or Example 49, wherein the second jaw includes a side surface extending from the compression surface to the outer surface of the second jaw, and the side surface includes a recess for receiving the device for applying the expansion force to the spring.

Example 51: The method of any example herein, in particular Examples 41-50, wherein: the spring includes a loop extending proximally towards the second end portion of the first jaw and the second end portion of the second jaw, the second end portion of the first jaw protrudes proximally from or is positioned at the loop, and the second end portion of the second jaw protrudes proximally from or is positioned at the loop.

Example 52: The method of any example herein, in particular Examples 41-51, wherein: the first jaw includes a side surface extending from the compression surface to the outer surface of the first jaw, and the side surface is curved concave relative to the first jaw, and the second jaw includes a side surface extending from the compression surface to the outer surface of the second jaw, and the side surface of the second jaw is curved concave relative to the second jaw.

Example 53: The method of any example herein, in particular Example 52, wherein: the side surface of the first jaw comprises a first side surface facing a first side direction, and the first jaw includes a second side surface facing opposite the first side surface and being curved convex relative to the first jaw, and the side surface of the second jaw comprises a third side surface facing the first side direction, and the second jaw includes a fourth side surface facing opposite the third side surface and being curved convex relative to the second jaw.

Example 54: The method of any example herein, in particular Example 52, wherein: the side surface of the first jaw comprises a first side surface facing a first side direction, and the first jaw includes a second side surface facing opposite the first side surface and being curved concave relative to the first jaw, and the side surface of the second jaw comprises a third side surface facing the first side direction, and the second jaw includes a fourth side surface facing opposite the third side surface and being curved concave relative to the second jaw.

Example 55: The method of any example herein, in particular Examples 52-54, wherein the side surface of the first jaw has a constant curvature, and the side surface of the second jaw has a constant curvature.

Example 56: The method of any example herein, in particular Examples 52-55, wherein the side surface of the first jaw is curved concave relative to the first jaw from a proximal tip of the first jaw to a distal tip of the first jaw.

Example 57: The method of any example herein, in particular Examples 41-56, wherein the spring has an outer surface, an inner surface, a first side surface extending from the outer surface to the inner surface and facing a first side direction, and a second side surface extending from the outer surface to the inner surface and facing a second side direction that is opposite the first side direction, and the first side surface is curved concave relative to the spring.

Example 58: The method of any example herein, in particular Example 57, wherein the second side surface is curved convex relative to the spring.

Example 59: The method of any example herein, in particular Examples 41-58, wherein: the outer surface of the first jaw includes a channel that is curved in a plane transverse to a plane of closure of the clip, the outer surface of the second jaw includes a channel that is curved in a plane transverse to the plane of closure of the clip, and the spring is curved in a plane transverse to the plane of closure of the clip and extends within the channel of the first jaw and the channel of the second jaw.

Example 60: The method of any example herein, in particular Examples 41-59, wherein the spring includes: a distal end portion having a height in a plane of closure of the clip and including a first end coupled to the first jaw and a second end coupled to the second jaw, and a proximal end portion having a height in the plane of closure of the clip and including a loop extending towards the second end portion of the first jaw and the second end portion of the second jaw, and wherein the height of the proximal end portion of the spring is greater than the height of the distal end portion of the spring.

Example 61: The method of any example herein, in particular Example 60, wherein the spring comprises a C-shaped spring surrounding an opening, and wherein a diameter of the opening at the proximal end portion of the spring is greater than a diameter of the opening at the distal end portion of the spring.

Example 62: The method of any example herein, in particular Example 60 or Example 61, wherein the proximal end portion of the spring is raised above the outer surface of the first jaw and is raised above the outer surface of the second jaw.

Example 63: The method of any example herein, in particular Examples 60-62, wherein the outer surface of the first jaw is at or is raised above the distal end portion of the spring, and the outer surface of the second jaw is at or is raised above the distal end portion of the spring.

Example 64: The method of any example herein, in particular Examples 41-63, wherein the second end portion of the first jaw is tapered, and the second end portion of the second jaw is tapered.

Example 65: The method of any example herein, in particular Examples 41-64, wherein the first end portion of the first jaw includes a distal tip and a first side wall and a second side wall and a gap between the first side wall and the second side wall, and the first side wall and the second side wall diverge away from each other in a direction towards the distal tip.

Example 66: The method of any example herein, in particular Example 65, wherein a width of the gap increases in a direction towards the distal tip.

Example 67: The method of any example herein, in particular Examples 41-66, wherein the second end portion of the first jaw includes a proximal tip and a first side wall and a second side wall and a gap between the first side wall and the second side wall, and the first side wall and the second side wall diverge away from each other in a direction towards the proximal tip.

Example 68: The method of any example herein, in particular Example 67, wherein a width of the gap increases in a direction towards the proximal tip.

Example 69: The method of any example herein, in particular Examples 41-68, wherein the compression surface of the first jaw includes a cushion layer.

Example 70: The method of any example herein, in particular Example 69, wherein the cushion layer is received within a track of the first jaw.

Example 71: The method of any example herein, in particular Example 69 or Example 70, wherein the first jaw includes one or more apertures for receiving the cushion layer.

Example 72: The method of any example herein, in particular Examples 69-71, wherein the cushion layer includes an elongate channel extending along the cushion layer.

Example 73: The method of any example herein, in particular Examples 69-72, wherein the cushion layer comprises an overmolding upon a portion of the first jaw.

Example 74: The method of any example herein, in particular Examples 69-73, wherein the compression surface of the second jaw includes a cushion layer.

Example 75: The method of any example herein, in particular Examples 41-74, further comprising one or more sleeves covering the first jaw and the second jaw.

Example 76: The method of any example herein, in particular Example 75, wherein a single sleeve covers the first jaw and the second jaw.

Example 77: The method of any example herein, in particular Example 75, wherein a first sleeve covers the first jaw and a second sleeve covers the second jaw.

Example 78: The method of any example herein, in particular Examples 75-77, wherein the one or more sleeves cover the spring.

Example 79: The method of any example herein, in particular Examples 75-78, further comprising one or more plugs positioned at the first end portion of the first jaw and coupled to the one or more sleeves.

Example 80: The method of any example herein, in particular Examples 75-79, further comprising one or more sutures positioned at the first end portion of the first jaw and coupled to the one or more sleeves.

Any of the features of any of the examples, including but not limited to any of the first through 80th examples referred to above, is applicable to all other aspects and examples identified herein, including but not limited to any examples of any of the first through 80th examples referred to above. Moreover, any of the features of an example of the various examples, including but not limited to any examples of any of the first through 80th examples referred to above, is independently combinable, partly or wholly with other examples described herein in any way, e.g., one, two, or three or more examples may be combinable in whole or in part. Further, any of the features of the various examples, including but not limited to any examples of any of the first through 80th examples referred to above, may be made optional to other examples. Any example of a method can be performed by a system or apparatus of another example, and any aspect or example of a system or apparatus can be configured to perform a method of another aspect or example, including but not limited to any examples of any of the first through 80th examples referred to above.

Certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as any subcombination or variation of any subcombination.

Moreover, while methods may be depicted in the drawings or described in the specification in a particular order, such methods need not be performed in the particular order shown or in sequential order, and that all methods need not be performed, to achieve desirable results. Other methods that are not depicted or described can be incorporated in the example methods and processes. For example, one or more additional methods can be performed before, after, simultaneously, or between any of the described methods. Further, the methods may be rearranged or reordered in other implementations. Also, the separation of various system components in the implementations described above should not be understood as requiring such separation in all implementations, and it should be understood that the described components and systems can generally be integrated together in a single product or packaged into multiple products. Additionally, other implementations are within the scope of this disclosure.

Conditional language, such as "can," "could," "might," or "may," unless specifically stated otherwise, or otherwise understood within the context as used, is generally intended to convey that certain examples include or do not include, certain features, elements, and/or steps. Thus, such conditional language is not generally intended to imply that features, elements, and/or steps are in any way required for one or more examples.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain examples require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than or equal to 10% of, within less than or equal to 5% of, within less than or equal to 1% of, within less than or equal to 0.1% of, and within less than or equal to 0.01% of the stated amount. If the stated amount is 0 (e.g., none, having no), the above recited ranges can be specific ranges, and not within a particular % of the value. For example, within less than or equal to 10 wt./vol. % of, within less than or equal to 5 wt./vol. % of, within less than or equal to 1 wt./vol. % of, within less than or equal to 0.1 wt./vol. % of, and within less than or equal to 0.01 wt./vol. % of the stated amount.

Some examples have been described in connection with the accompanying drawings. The figures are drawn to scale, but such scale should not be limiting, since dimensions and proportions other than what are shown are contemplated and are within the scope of the disclosure. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various examples can be used in all other examples set forth herein. Additionally, it will be recognized that any methods described herein may be practiced using any device suitable for performing the recited steps.

While a number of examples and variations thereof have been described in detail, other modifications and methods of using the same will be apparent to those of skill in the art. Accordingly, it should be understood that various applications, modifications, materials, and substitutions can be made of equivalents without departing from the unique and inventive disclosure herein or the scope of the claims.

What is claimed is:

1. A clip for a portion of a heart, the clip comprising:
a first jaw extending from a first end portion to a second end portion and including a compression surface and an outer surface facing opposite the compression surface, the first jaw including a side surface extending from the compression surface to the outer surface of the first jaw, at least a portion of the side surface being curved concave relative to the first jaw;
a second jaw extending from a first end portion to a second end portion and including a compression surface facing the compression surface of the first jaw and an outer surface facing opposite the compression surface of the second jaw, the second jaw including a side surface extending from the compression surface of the second jaw to the outer surface of the second jaw, at least a portion of the side surface of the second jaw being curved concave relative to the second jaw; and
a spring extending over the outer surface of the first jaw and the outer surface of the second jaw and configured to force the first jaw and the second jaw together to compress the portion of the heart between the compression surface of the first jaw and the compression surface of the second jaw, and
wherein the side surface of the first jaw includes a recess for receiving a device for applying an expansion force to the spring.

2. The clip of claim 1, wherein:
the first jaw includes a central portion between the first end portion and the second end portion of the first jaw;
the second jaw includes a central portion between the first end portion and the second end portion of the second jaw; and
the spring includes a first end coupled to the central portion of the first jaw and a second end coupled to the central portion of the second jaw.

3. The clip of claim 2, wherein the spring includes a loop extending towards the second end portion of the first jaw and the second end portion of the second jaw.

4. The clip of claim 3, wherein:
the outer surface of the first jaw includes a channel;
the outer surface of the second jaw includes a channel; and
the loop extends within the channel of the first jaw and the channel of the second jaw.

5. The clip of claim 3, wherein the loop protrudes from the second end portion of the first jaw and the second end portion of the second jaw.

6. The clip of claim 1, wherein the first end portion of the first jaw is tapered, and the second end portion of the first jaw is tapered.

7. The clip of claim 1, wherein the recess is positioned between a first end of the spring and the second end portion of the first jaw.

8. The clip of claim 1, wherein the side surface of the second jaw includes a recess for receiving the device for applying the expansion force to the spring.

9. The clip of claim 1, wherein:
the spring includes a loop extending proximally towards the second end portion of the first jaw and the second end portion of the second jaw;
the second end portion of the first jaw protrudes proximally from or is positioned at the loop; and the second end portion of the second jaw protrudes proximally from or is positioned at the loop.

10. The clip of claim 1, wherein:

the side surface of the first jaw comprises a first side surface facing a first side direction, and the first jaw includes a second side surface facing opposite the first side surface, with at least a portion of the second side surface being curved concave relative to the first jaw; and the side surface of the second jaw comprises a third side surface facing the first side direction, and the second jaw includes a fourth side surface facing opposite the third side surface, with at least a portion of the fourth side surface being curved concave relative to the second jaw.

11. The clip of claim 1, wherein at least the portion of the side surface of the first jaw is curved concave relative to the first jaw from a proximal tip of the first jaw to a distal tip of the first jaw.

12. The clip of claim 1, wherein the spring has an outer surface, an inner surface, a first side surface extending from the outer surface to the inner surface and facing a first side direction, and a second side surface extending from the outer surface to the inner surface and facing a second side direction that is opposite the first side direction, and at least the portion of the side surface of the first jaw is curved concave relative to the spring.

13. The clip of claim 1, wherein the spring includes:

a distal end portion having a height in a plane of closure of the clip and including a first end coupled to the first jaw and a second end coupled to the second jaw; and a proximal end portion having a height in the plane of closure of the clip and including a loop extending towards the second end portion of the first jaw and the second end portion of the second jaw, and wherein the height of the proximal end portion of the spring is greater than the height of the distal end portion of the spring.

14. The clip of claim 13, wherein the spring comprises a C-shaped spring surrounding an opening, and wherein a diameter of the opening at the proximal end portion of the spring is greater than a diameter of the opening at the distal end portion of the spring.

15. The clip of claim 13, wherein the proximal end portion of the spring is raised above the outer surface of the first jaw and is raised above the outer surface of the second jaw.

16. The clip of claim 13, wherein the outer surface of the first jaw is at or is raised above the distal end portion of the spring, and the outer surface of the second jaw is at or is raised above the distal end portion of the spring.

17. The clip of claim 1, wherein the second end portion of the first jaw is tapered, and the second end portion of the second jaw is tapered.

18. The clip of claim 1, wherein the compression surface of the first jaw includes a cushion layer.

19. The clip of claim 1, wherein the clip is configured to occlude a left atrial appendage.

20. A clip for a portion of a heart, the clip comprising:

a first jaw extending from a first end portion to a second end portion and including a compression surface and an outer surface facing opposite the compression surface, the first jaw including a side surface extending from the compression surface to the outer surface of the first jaw, at least a portion of the side surface being curved concave relative to the first jaw;

a second jaw extending from a first end portion to a second end portion and including a compression surface facing the compression surface of the first jaw and an outer surface facing opposite the compression surface of the second jaw, the second jaw including a side surface extending from the compression surface of the second jaw to the outer surface of the second jaw, at least a portion of the side surface of the second jaw being curved concave relative to the second jaw;

a spring extending over the outer surface of the first jaw and the outer surface of the second jaw and configured to force the first jaw and the second jaw together to compress the portion of the heart between the compression surface of the first jaw and the compression surface of the second jaw, wherein the spring includes:

a distal end portion having a height in a plane of closure of the clip and including a first end coupled to the first jaw and a second end coupled to the second jaw, and a proximal end portion having a height in the plane of closure of the clip and including a loop extending towards the second end portion of the first jaw and the second end portion of the second jaw, and wherein the height of the proximal end portion of the spring is greater than the height of the distal end portion of the spring; and wherein the outer surface of the first jaw is at or is raised above the distal end portion of the spring, and the outer surface of the second jaw is at or is raised above the distal end portion of the spring.

* * * * *